United States Patent
Pinter et al.

(10) Patent No.: US 9,571,789 B2
(45) Date of Patent: *Feb. 14, 2017

(54) ENHANCED VIDEO INTERACTION FOR A USER INTERFACE OF A TELEPRESENCE NETWORK

(71) Applicant: INTOUCH TECHNOLOGIES, INC., Goleta, CA (US)

(72) Inventors: Marco Pinter, Santa Barbara, CA (US); Charles S. Jordan, Mill Spring, NC (US); Daniel Sanchez, Summerland, CA (US); Kevin Hanrahan, Santa Barbara, CA (US); Kelton Temby, Santa Barbara, CA (US); Christopher Lambrecht, Santa Barbara, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/747,839

(22) Filed: Jun. 23, 2015

(65) Prior Publication Data

US 2015/0296177 A1 Oct. 15, 2015

Related U.S. Application Data

(63) Continuation of application No. 13/830,334, filed on Mar. 14, 2013, now Pat. No. 9,098,611.

(Continued)

(51) Int. Cl.
*H04N 7/14* (2006.01)
*G06F 19/00* (2011.01)
*H04N 7/18* (2006.01)

(52) U.S. Cl.
CPC .......... *H04N 7/147* (2013.01); *G06F 19/3418* (2013.01); *H04N 7/142* (2013.01); *H04N 7/181* (2013.01); *H04N 7/185* (2013.01)

(58) Field of Classification Search
CPC ........ H04N 7/147; H04N 7/181; H04N 7/185; G06F 19/3418

(Continued)

(56) References Cited

U.S. PATENT DOCUMENTS 5,734,804 A 3/1998 Bergner
6,006,140 A * 12/1999 Carter .................. G02B 21/367
382/133

(Continued)

FOREIGN PATENT DOCUMENTS

JP 08-166822 A 6/1996
JP 2006-035381 A 2/2006

OTHER PUBLICATIONS

Fulbright et al., "SWAMI: An Autonomous Mobile Robot for Inspection of Nuclear Waste of Storage Facilities", Autonomous Robots, 2, 1995, pp. 225-235.

*Primary Examiner* — Gerald Gauthier

(57) ABSTRACT

A telepresence device may relay video, audio, and/or measurement data to a user operating a control device. A user interface may permit the user to quickly view and/or understand temporally and/or spatially disparate information. The telepresence device may pre-gather looped video of spatially disparate areas in an environment. A temporal control mechanism may start video playback at a desired point in a current or historical video segment. Notations may be associated with time spans in a video and recalled by capturing an image similar to a frame in the time span of the video. An area of interest may be selected and video containing the area of interest may be automatically found. Situational data may be recorded and used to recall video segments of interest. The telepresence device may synchronize video (Continued)

playback and movement. A series of videos may be recorded at predetermined time intervals to capture visually trending information.

41 Claims, 18 Drawing Sheets

Related U.S. Application Data

(60) Provisional application No. 61/729,964, filed on Nov. 26, 2012.

(58) Field of Classification Search
USPC ............. 345/671; 348/14.03, 14.05, 61, 150, 348/218.1, 14.01, 14.02; 376/249; 382/103, 382/173, 195; 700/56, 259; 709/227; 715/855; 706/11
See application file for complete search history.

(56) References Cited

U.S. PATENT DOCUMENTS

| | | | |
|---|---|---|---|
| 6,342,915 B1* | 1/2002 | Ozaki | H04N 7/18 340/505 |
| 6,411,055 B1 | 6/2002 | Fujita et al. | |
| 6,667,592 B2 | 12/2003 | Jacobs et al. | |
| 6,674,259 B1 | 1/2004 | Norman et al. | |
| 6,856,662 B2* | 2/2005 | Glass | G21C 17/003 374/5 |
| 7,123,292 B1* | 10/2006 | Seeger | G03B 5/02 348/218.1 |
| 7,467,211 B1 | 12/2008 | Herman et al. | |
| 7,483,867 B2 | 1/2009 | Ansari et al. | |
| 8,401,229 B2* | 3/2013 | Hassan-Shafique | G06K 9/00771 348/50 |
| 8,612,051 B2 | 12/2013 | Norman et al. | |
| 8,620,077 B1* | 12/2013 | Grundmann | G06K 9/00765 382/164 |
| 8,712,162 B2* | 4/2014 | Kirsch | G06K 9/4619 382/195 |
| 8,718,837 B2 | 5/2014 | Wang et al. | |
| 8,965,579 B2 | 2/2015 | Wang | |
| 9,219,857 B2* | 12/2015 | Eldon | H04N 5/23219 |
| 9,224,181 B2* | 12/2015 | Pinter | G06F 19/327 |
| 2004/0140404 A1 | 7/2004 | Ohta et al. | |
| 2004/0260790 A1 | 12/2004 | Balloni et al. | |
| 2005/0278446 A1* | 12/2005 | Bryant | H04L 29/06027 709/227 |
| 2006/0184274 A1 | 8/2006 | Sakai et al. | |
| 2007/0016328 A1 | 1/2007 | Ziegler et al. | |
| 2007/0109324 A1* | 5/2007 | Lin | H04N 5/4403 345/671 |
| 2008/0056933 A1 | 3/2008 | Moore et al. | |
| 2008/0263628 A1 | 10/2008 | Norman et al. | |
| 2009/0146882 A1 | 6/2009 | Halivaara et al. | |
| 2009/0201372 A1* | 8/2009 | O'Doherty | G07F 19/20 348/150 |
| 2010/0128104 A1 | 5/2010 | Fabregat et al. | |
| 2011/0288417 A1 | 11/2011 | Pinter et al. | |
| 2012/0182392 A1 | 7/2012 | Kearns et al. | |
| 2013/0002794 A1* | 1/2013 | Hines | H04L 65/4076 348/14.01 |
| 2013/0113871 A1* | 5/2013 | Ballantyne | A61B 5/7465 348/14.05 |
| 2013/0275922 A1* | 10/2013 | Pinter | G06F 19/327 715/855 |
| 2013/0325244 A1 | 12/2013 | Wang et al. | |
| 2014/0015914 A1* | 1/2014 | Delaunay | H04N 7/15 348/14.02 |
| 2014/0207286 A1 | 7/2014 | Wang et al. | |
| 2014/0267549 A1* | 9/2014 | Pinter | G06F 19/3418 348/14.03 |
| 2015/0077502 A1 | 3/2015 | Jordan et al. | |
| 2015/0081338 A1 | 3/2015 | Lai et al. | |
| 2015/0088310 A1 | 3/2015 | Pinter et al. | |

* cited by examiner

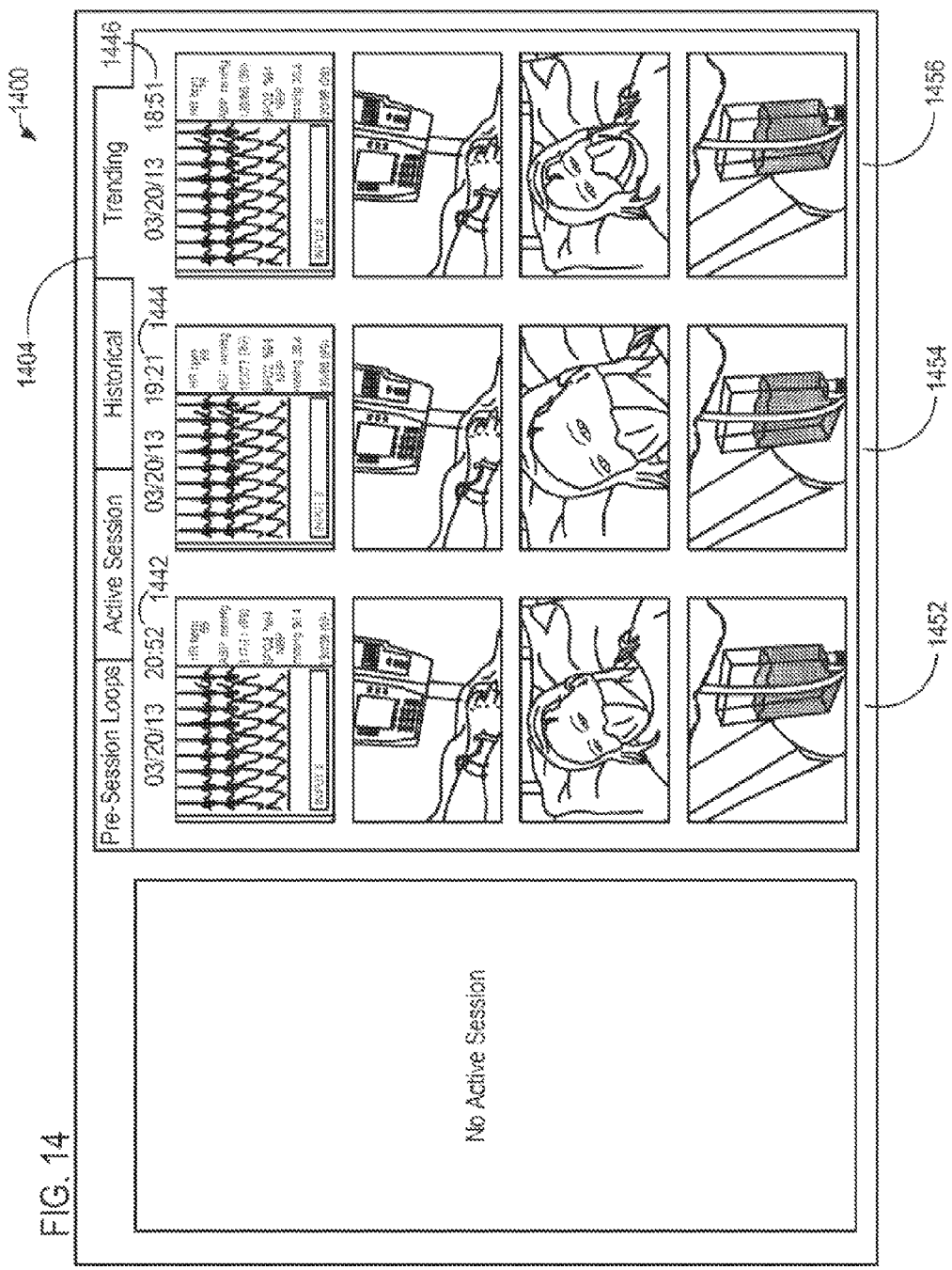

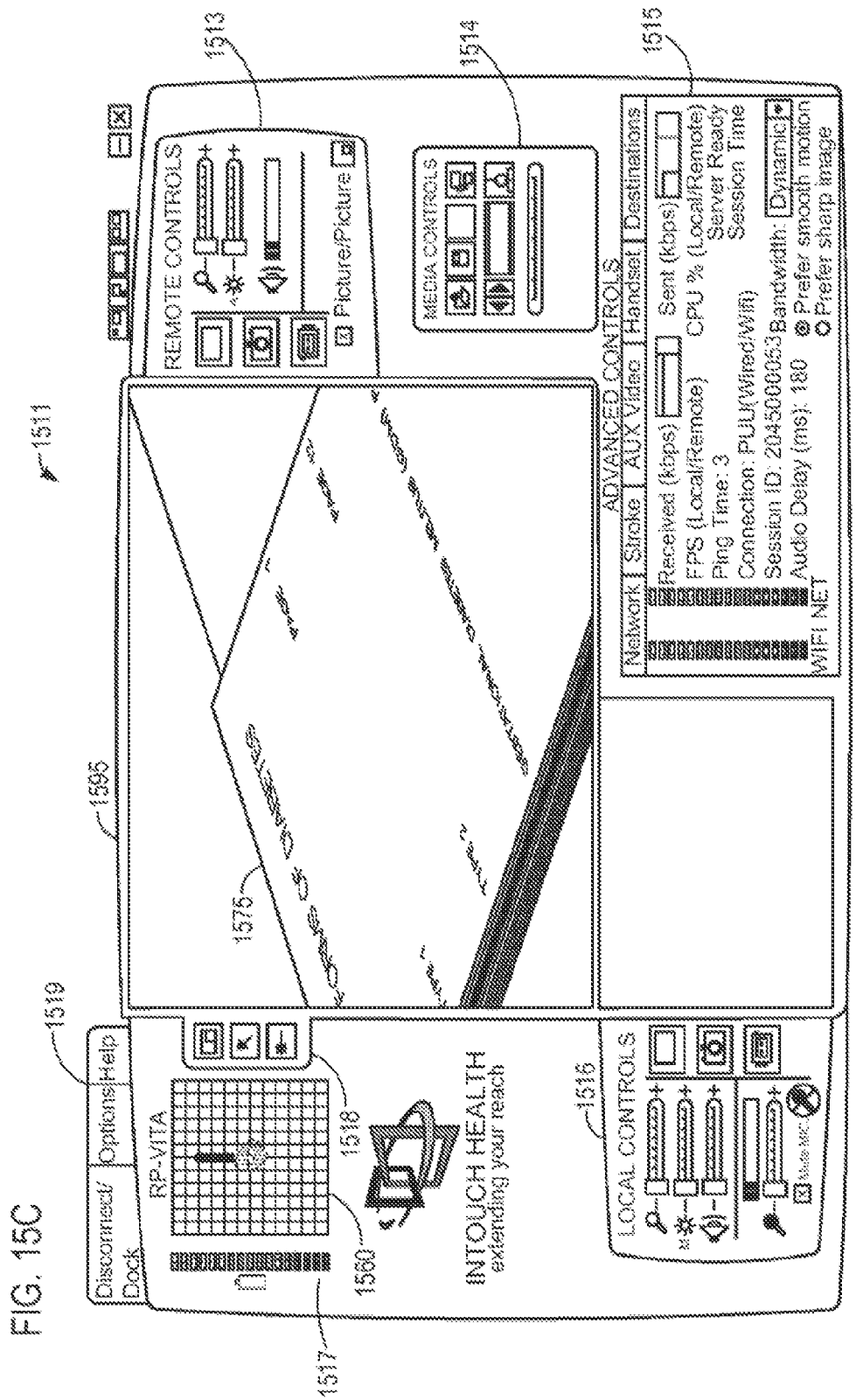

ENHANCED VIDEO INTERACTION FOR A USER INTERFACE OF A TELEPRESENCE NETWORK

CROSS-REFERENCE TO RELATED APPLICATIONS

This application is a continuation of U.S. patent application Ser. No. 13/830,334, filed on Mar. 14, 2013, now U.S. Pat. No. 9,098,611.

GOVERNMENT LICENSE RIGHTS

This invention was made with government support under grant number R43 MD006709 awarded by the National Institutes of Health. The government has certain rights in the invention.

TECHNICAL FIELD

This disclosure relates to enhanced interactive and display interfaces for a telepresence device. More specifically, this disclosure relates to systems and methods for improving user access and understanding of spatially and/or temporally disparate information contained in saved video captured by a telepresence device.

BRIEF DESCRIPTION OF THE DRAWINGS

Non-limiting and non-exhaustive embodiments of the disclosure are described herein, including various embodiments of the disclosure illustrated in the figures listed below.

FIG. 14 is an exemplary screen display a series of stored trend videos for a plurality of areas of interest.

FIG. 15C illustrates a zoomed view of the document with the text at an angle and skewed.

Figure 1:
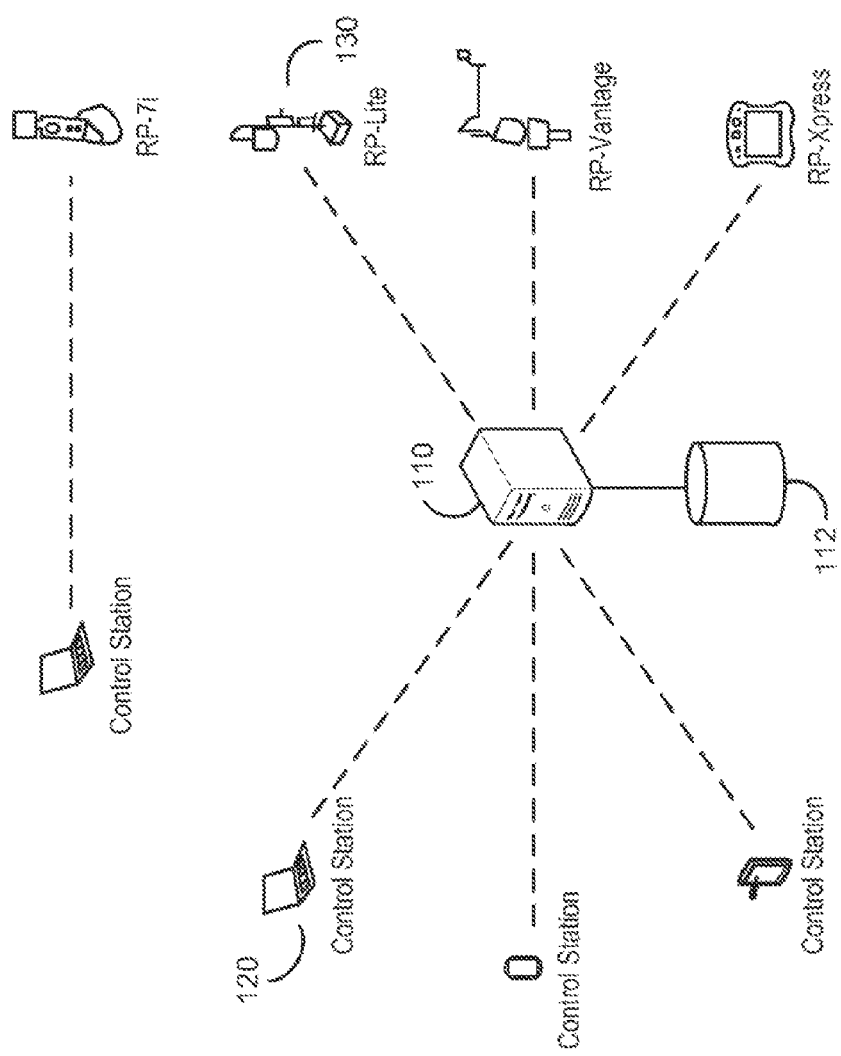
FIG. 1 is a schematic diagram of a telepresence network comprising a plurality of telepresence devices.

The described features, structures, and/or characteristics of the systems and methods described herein may be combined in any suitable manner in one or more alternative embodiments, and may differ from the illustrated embodiments.

DETAILED DESCRIPTION OF PREFERRED EMBODIMENTS

A telepresence device may be part of a telepresence network that allows users remote from the telepresence device to interact with an environment where the telepresence device is located. The telepresence device may be configured to capture video and/or environmental measurements, which may be relayed to one or more users. A control device may allow the one or more users to interact with the telepresence device, such as by sending and/or receiving captured video and/or audio, sending commands to the telepresence device, and the like. Each telepresence network may include one or more facilities that each include at least one corresponding telepresence device local to the facility. Exemplary facilities may include manufacturing plants, research and development facilities, testing facilities, hospitals, rehabilitation facilities, long-term care facilities, and the like. Types of telepresence devices include, but are not limited to, remote telepresence devices, mobile telepresence units, and/or control stations. For example, a remote telepresence device may include a telepresence robot configured to move within a medical facility and provide a means for a remote practitioner to perform remote consultations.

Exemplary, non-limiting uses for telepresence devices may include healthcare and industrial applications. For example, healthcare facilities may include telemedicine technologies, such as telepresence devices in a telepresence network, that allow remote healthcare practitioners to provide services to patients and/or other healthcare practitioners in remote locations. A remote medical professional may be a neurologist practicing in a relatively large hospital who may, via a telepresence device, provide services and consultations to patients and/or other medical professionals in hospitals located in rural areas that otherwise may not have a neurologist on staff.

The control device may include a general purpose and/or special purpose computer systems and/or one or more computer networks. In an embodiment, the control device and the telepresence device may each include at least one camera, at least one display device, at least one speaker, and at least one microphone to allow for two-way video/audio communication. One or more input devices may allow the user of the control device to remotely control movement of the telepresence device. Additional discussion of remotely controlling movement of a telepresence device is contained in U.S. Pat. No. 6,845,297, titled "Method and System for Remote Control of Mobile Robot," filed on Jan. 9, 2003, and European Patent No. 1279081, titled "Method and System for Remote Control of Mobile Robot," filed on May 1, 2001, which applications are hereby incorporated by reference in their entireties.

The control device, the telepresence device, and/or the telepresence network may be configured to store session content data, such video and/or audio recordings, telemetry data, notes, time stamps, and/or the like. In an embodiment, the telepresence network may include a server configured to store the session content data. Addition discussion of data storage for telepresence devices and automatic use of stored data contained in U.S. patent application Ser. No. 12/362, 454, titled "DOCUMENTATION THROUGH A REMOTE PRESENCE ROBOT," filed on Jan. 29, 2009, which application is hereby incorporated by reference in its entirety.

Reference throughout this specification to "one embodiment" or "an embodiment" means that a particular feature, structure, or characteristic described in connection with the embodiment is included in at least one embodiment. Thus, the appearances of the phrases "in one embodiment" and "in an embodiment" in various places throughout this specification are not necessarily all referring to the same embodiment. In particular, an "embodiment" may be a system, an article of manufacture (such as a computer-readable storage medium), a method, and/or a product of a process.

The phrases "connected to" and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

The embodiments of the disclosure may be understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations and/or components are not shown or described in detail.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless otherwise specified.

Embodiments may include various steps, which may be embodied in machine-executable instructions to be executed by a computer system. The computer system may comprise one or more general-purpose or special-purpose computers (or other electronic devices). Alternatively, the computer system may comprise hardware components that include specific logic for performing the steps or comprise a combination of hardware, software, and/or firmware. Without limitation, a computer system may comprise a workstation, desktop computer, laptop computer, disconnectable mobile computer, server, mainframe, cluster, so-called "network computer" or "thin client," tablet, smartphone, multimedia device, electronic reader, personal digital assistant or other handheld computing device, "smart" consumer electronics device or appliance, or a combination thereof. A server may include a physical server, a server cluster, a distributed server, a virtual server, a cloud server, a computer providing resources to one or more clients, a combination of one or more of the aforementioned, and/or the like. Some or all of the functions, steps, and/or operations discussed herein may be performed by one or more clients and/or one or more servers. Those of skill in the art will realize possible divisions of operations between the one or more servers and the one or more clients.

Each computer system includes at least a processor and a memory; computer systems may also include various input devices and/or output devices. The processor may include one or more general-purpose central processing units (CPUs), graphic processing units (GPUs), or Digital Signal Processors (DSPs), such as Intel®, AMD®, ARM®, Nvidia®, ATI®, TI®, or other "off-the-shelf" microprocessors. The processor may include a special-purpose processing device, such as an ASIC, PAL, PLA, PLD, Field Programmable Gate Array (FPGA), or other customized or programmable device. The memory may include static RAM, dynamic RAM, flash memory, ROM, CD-ROM, disk, tape, magnetic, optical, or other computer storage medium. The input device(s) may include a keyboard, mouse, touch screen, light or other pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computers may be capable of using a floppy drive, tape drive, optical drive, magneto-optical drive, memory card reader, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and predefined manner as described herein.

Embodiments may also be provided as a computer program product, including a non-transitory machine-readable storage medium having stored thereon instructions that may be used to program a computer system (or other electronic device) to perform processes described herein. The non-transitory machine-readable storage medium may include, but is not limited to, hard drives, floppy diskettes, optical disks, CD-ROMs, DVD-ROMs, ROMs, RAMs, EPROMs, EEPROMs, magnetic or optical cards, tapes, solid-state memory devices, or other types of media/machine-readable media suitable for storing electronic instructions.

Suitable networks for configuration and/or use as described herein include one or more local area networks, wide area networks, metropolitan area networks, and/or "Internet" or IP networks, such as the World Wide Web, a private Internet, a secure Internet, a value-added network, a virtual private network, an extranet, an intranet, or even standalone machines which communicate with other machines by physical transport of media (a so-called "sneakernet"). In particular, a suitable network may be formed from parts or entireties of two or more other networks, including networks using disparate hardware and network communication technologies. One suitable network includes a server and several clients; other suitable networks may contain other combinations of servers, clients, and/or peer-to-peer nodes, and a given computer may function both as a client and as a server. Each network includes at least two computer systems, such as the server and/or clients.

The network may include communications or networking software, such as the software available from Novell, Microsoft, Artisoft, and other vendors, and may operate using TCP/IP, SPX, IPX, and other protocols over twisted pair, coaxial, or optical fiber cables, telephone lines, satellites, microwave relays, modulated AC power lines, physical media transfer, and/or other data transmission "wires" known to those of skill in the art. The network may encompass smaller networks and/or be connectable to other networks through a gateway or similar mechanism.

Suitable software to assist in implementing the invention is readily provided by those of skill in the pertinent art(s) using the teachings presented here and programming languages and tools, such as Java, Pascal, C++, PHP, JavaScript, Python, C#, Perl, SQL, Ruby, Shell, Visual Basic, Assembly, Action Script, Objective C, Lisp, Scala, Tcl Haskell, Scheme, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer-executable code located within a memory device. A software module may, for instance, comprise one or more physical or logical blocks of computer instructions, which may be organized as a routine, a program, a script, an object, a component, a data structure, etc., that perform one or more tasks or Implements particular abstract data types.

In certain embodiments, a particular software module may comprise disparate instructions stored in different locations of a memory device, different memory devices, or different computers, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data be tied or rendered together in a database record may be resident in the same memory device, or across several memory devices, and may be linked together in fields of a record in a database across a network.

Much of the infrastructure that may be used according to the present invention is already available, such as general-purpose computers, computer programming tools and techniques, computer networks and networking technologies, and digital storage media.

FIG. 1 is a schematic diagram of a telepresence network 100 comprising a plurality of telepresence devices 130. A plurality of control devices 120, such as laptops, tablets, smart phones, and the like, may be configured to transmit video, audio, and/or commands to the telepresence devices 130 and receive video, audio, and/or measurement data from the telepresence devices 130. The control devices 120 may directly couple to the telepresence devices 130, and/or a server 110 may couple the control devices to the telepresence devices 130. In an embodiment, the server 110 may establish a connection between a control device 120 and a telepresence device 130, and the control device 120 and telepresence device 130 may communicate directly after the connection has been established. A connection between a control device 120 and a telepresence device 130 may be referred to as a session. The server 110 may comprise and/or be coupled to a hard drive 112. The hard drive 112 may be configured to store a history for one or more control devices 120 and/or telepresence devices 130. The history may include session data, commands, measurement data recorded video and/or audio, annotations, bookmarks, and the like. The control devices 120 may be able retrieve the history from the hard drive 112 via the server 110.

Figure 2:
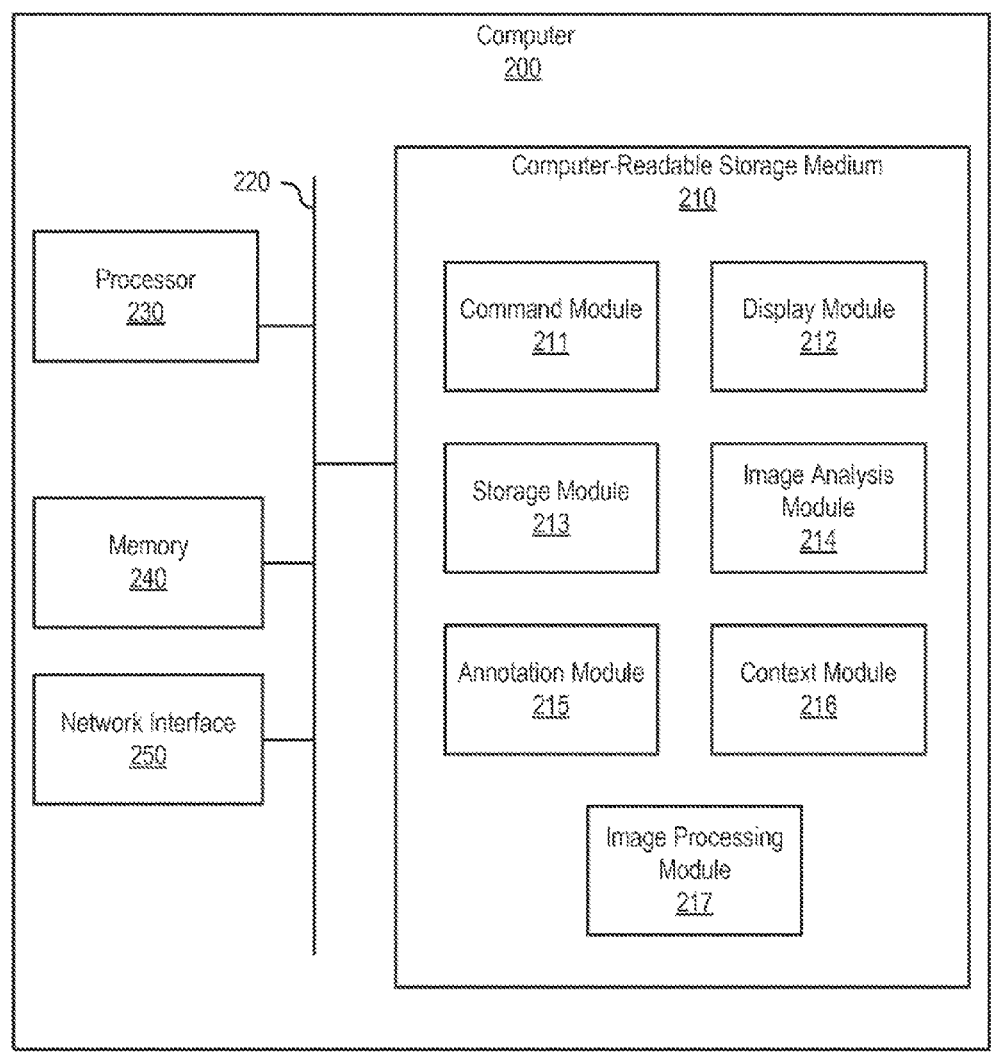
FIG. 2 is a schematic diagram of a computer configured to provide enhance video interaction.

FIG. 2 is a schematic diagram of a computer 200 configured to provide enhance video interaction. The computer 200 may include a processor 230 coupled to a volatile memory 240, a network interface 250, and a computer-readable storage medium 210 by a bus 220. In some embodiments, the computer-readable storage medium 210 may comprise the volatile memory 240. The computer-readable storage medium 210 may include a plurality of modules configured to perform specific functions, such as a command module 211 configured to deliver commands to a telepresence device, a display module 212 configured to provide a user interface for a user, a storage module 213 configured to store selected video, audio, and/or data, an image analysis module 214 configured to identify objects of interest in an image, an events module 215 configured to store events corresponding to time spans in videos, a context module 216 configured to store and search situational data, and an image processing module 217 edit, modify, and/or overlay images on a video. Alternatively, the computer 200 may contain more or fewer modules and/or a different computer may contain some of the modules.

Figure 3B:
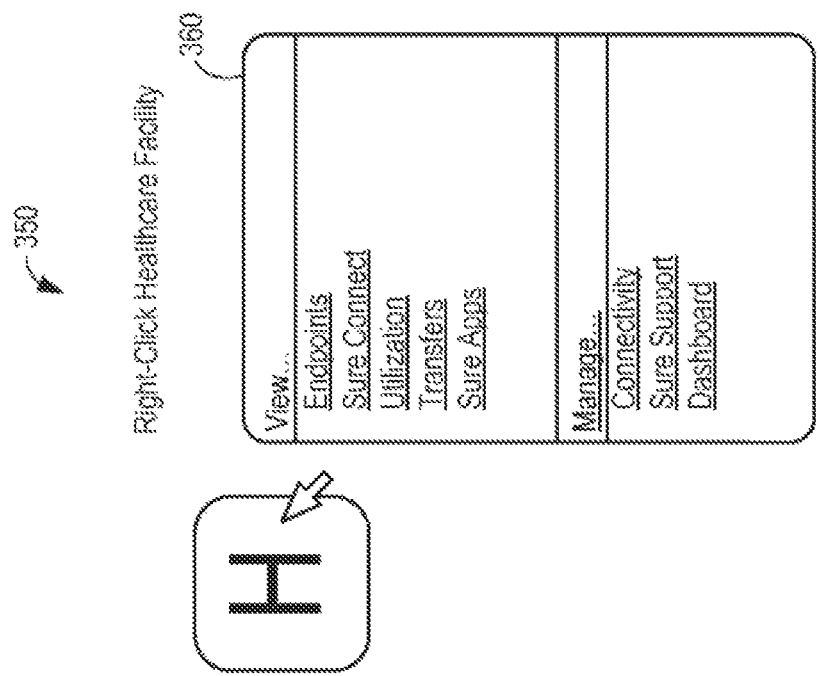
FIG. 3A,B are exemplary screen displays that may be displayed to a user of a control device.
Figure 3A:
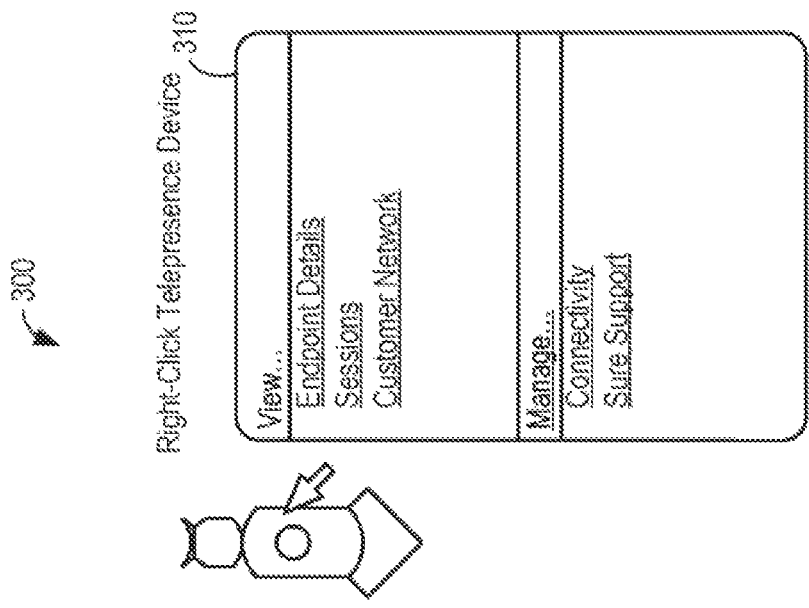

FIGS. 3A,B are exemplary screen displays 300, 350 that may be displayed to a user of a control device. The user may be attempting to connect to a telepresence device. A plurality of options 310, 360 may be displayed to the user including available endpoints to which the user may connect. The user may select the telepresence directly and/or select a healthcare facility or patient of interest. An optimal telepresence device may be automatically connected to if a healthcare facility or patient of interest is selected.

Figure 4:
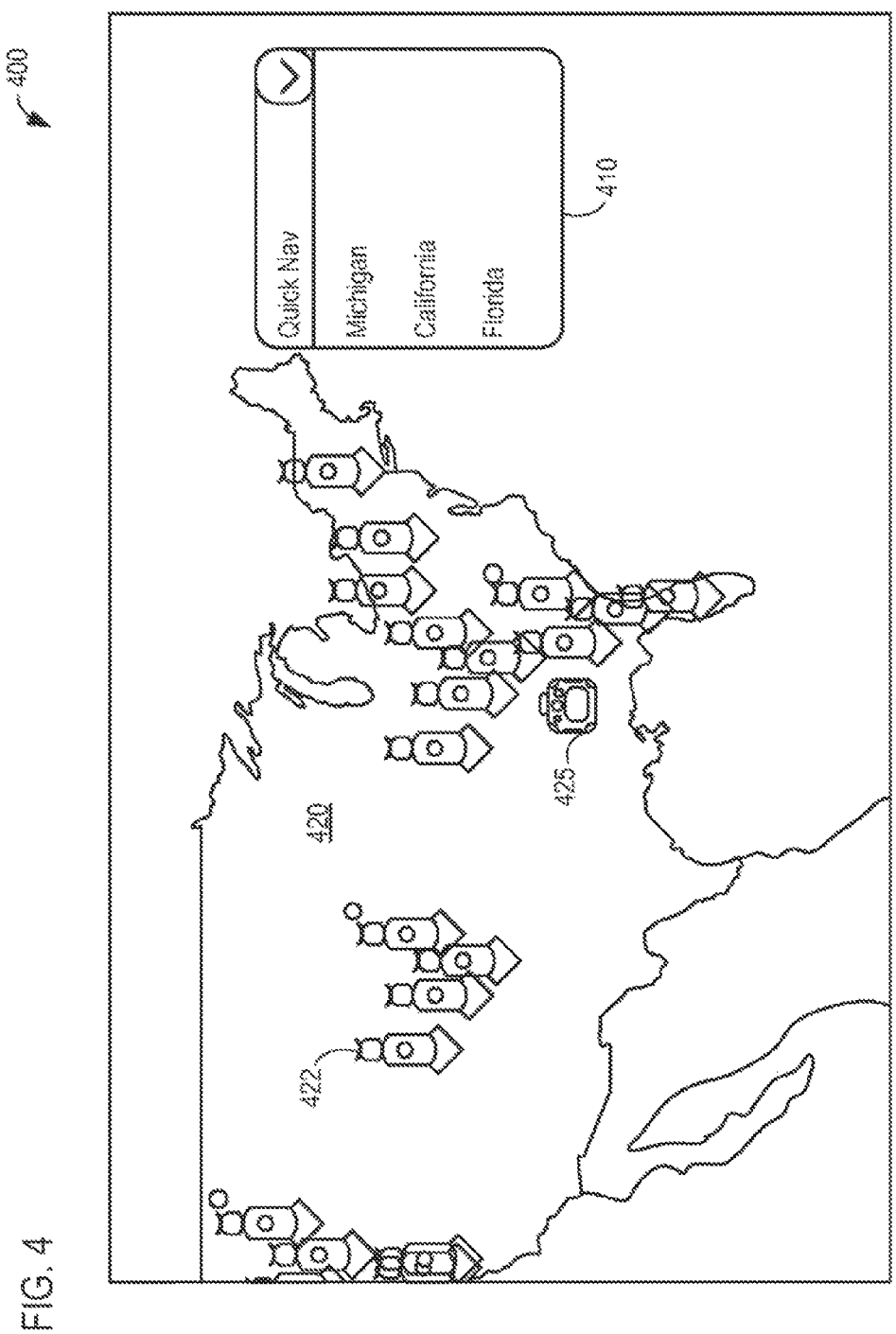
FIG. 4 is an exemplary screen display comprising a telepresence device location map.

FIG. 4 is an exemplary screen display 400 comprising a telepresence device location map 420. The locations of various telepresence devices 422, 425 may be illustrated as figures on the map 420. A Quick Nav bar 410 may allow the user to see telepresence devices available in a region of interest. The user may be able to connect to one of the telepresence devices 422, 425 by selecting the desired telepresence device from the map 420.

Figure 5:
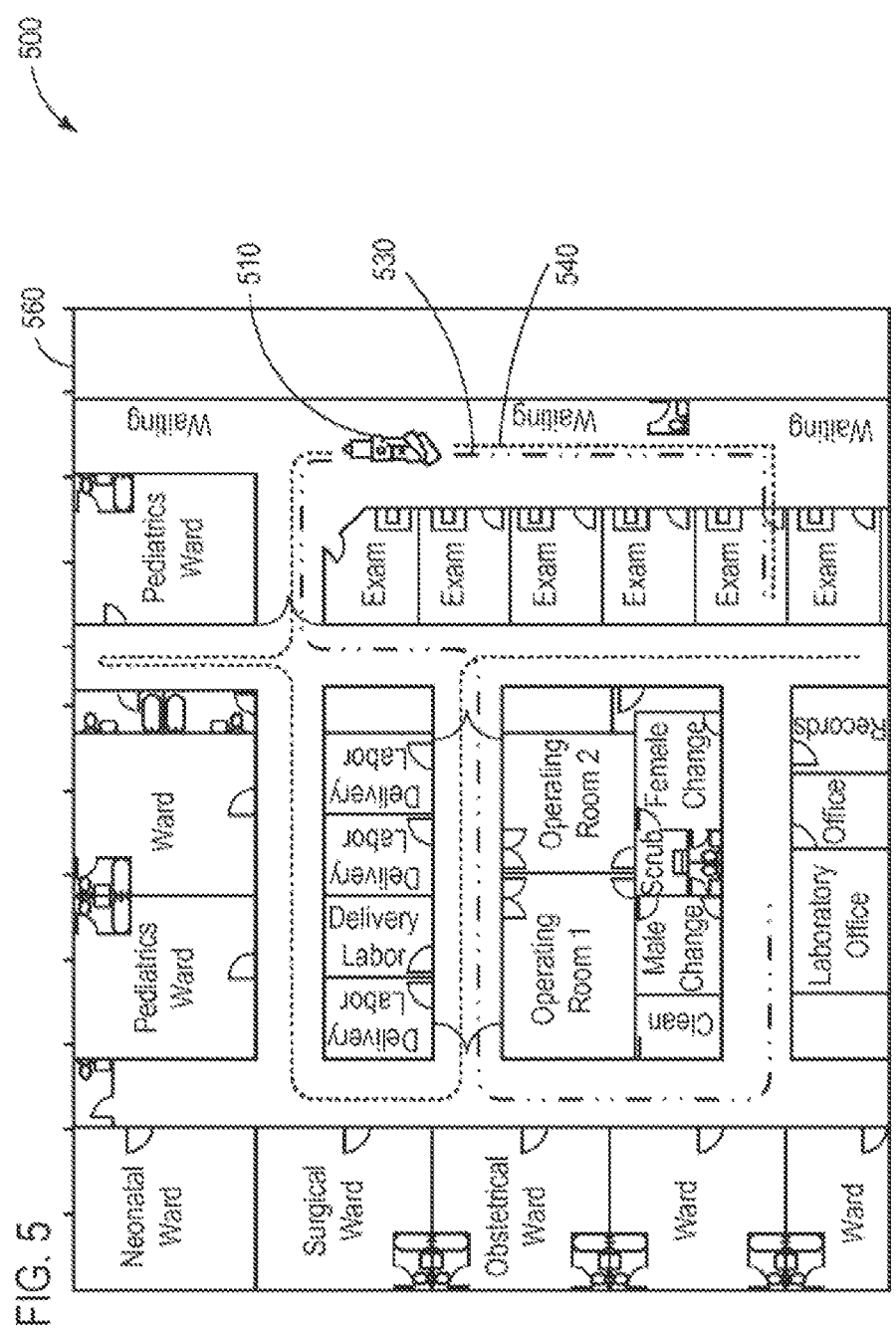
FIG. 5 is an exemplary screen display of a healthcare facility map.

FIG. 5 is an exemplary screen display 500 of a healthcare facility map 560. The healthcare facility map 560 may be displayed to the user upon initially connecting to telepresence device 510. The user may be able to automatically and/or manually navigate the telepresence device 510 to the location of a patient of interest. The healthcare facility map 560 may indicate a previously travelled route 540 and a route 530 currently being travelled by the telepresence device 510. In some embodiments, movement of the telepresence device 510 may be controlled by a central server (e.g., the server 110).

Figure 6:
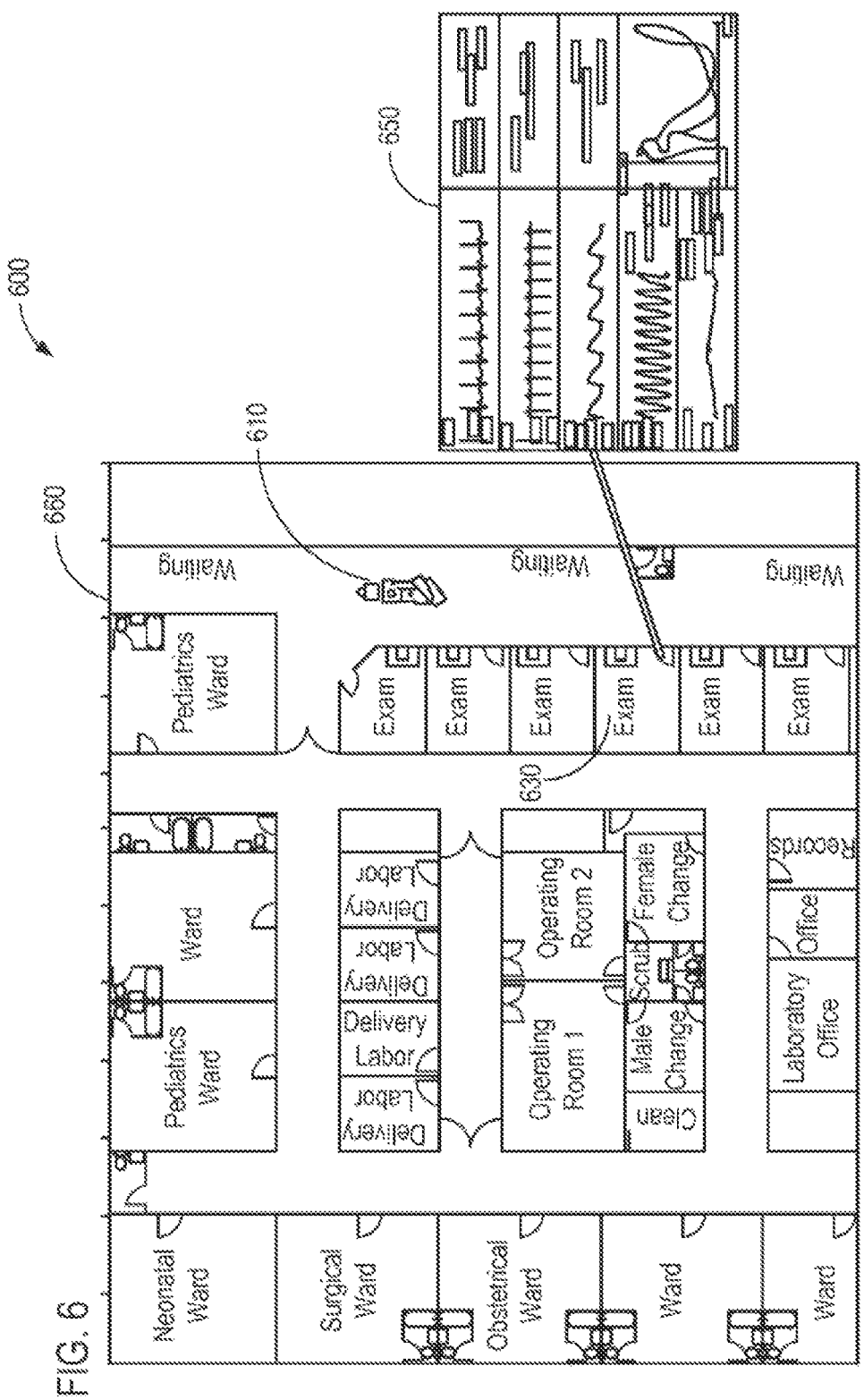
FIG. 6 is an exemplary screen display of an interactive healthcare facility map.

FIG. 6 is an exemplary screen display 600 of an interactive healthcare facility map 660. The interactive health care facility map 660 may allow a use to view patient information and/or telemetry data 650 while waiting for the telepresence device 610 to reach a destination. The telemetry data 650 may include physiological parameters displayed graphically and/or as numerical values. The user may view the patient information and/or telemetry data 650 by selecting a room 630 and/or patient of interest. In other embodiments, the user may be able to view only the patient information and/or telemetry data 650 from a patient being visited by the telepresence device or may not be permitted to see any patient information or telemetry data 650. For a patient being visited, the patient information and/or telemetry data 650 may be automatically displayed and/or manually requested by the user.

Figure 7:
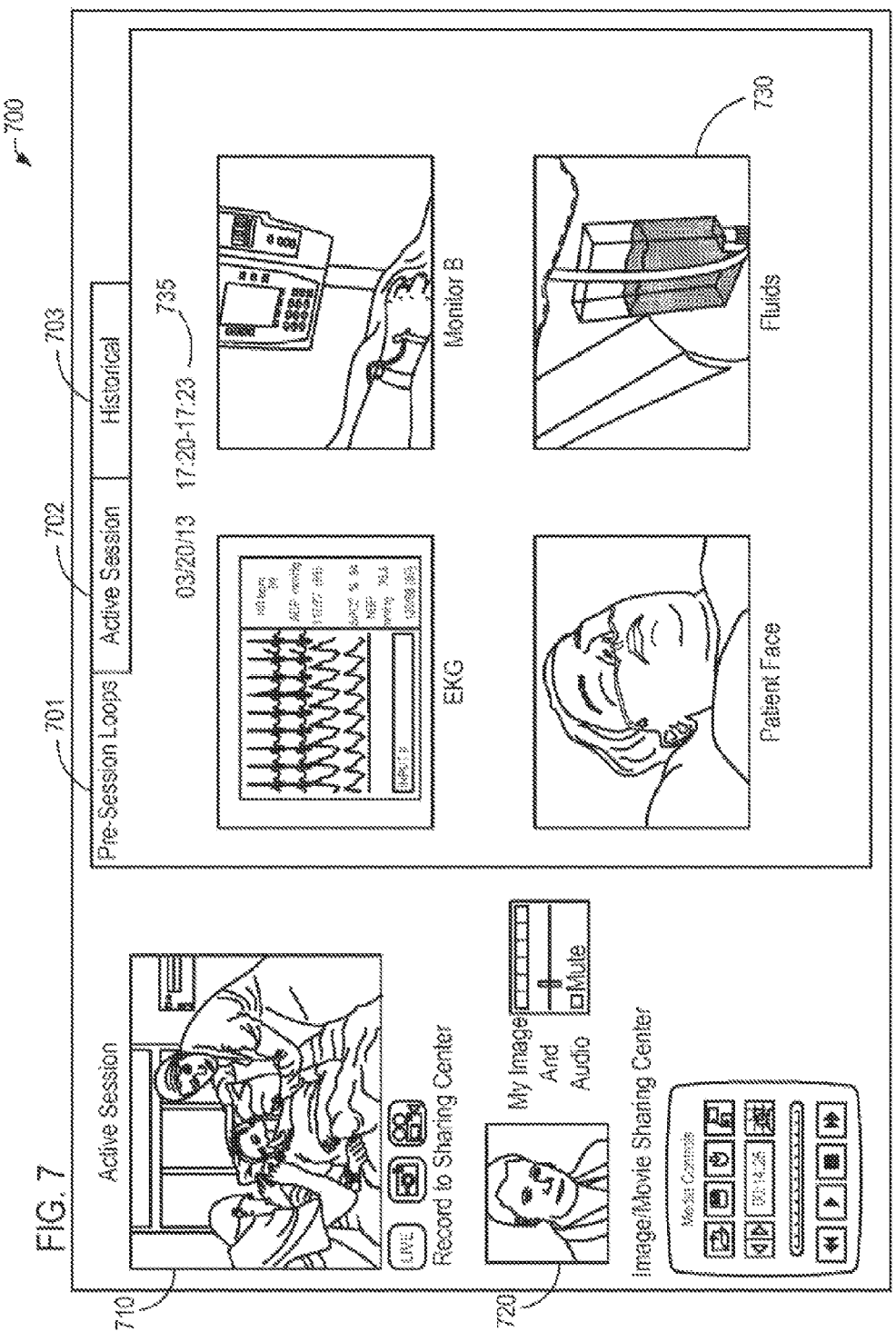
FIG. 7 is an exemplary screen display that may be seen by the user during a session with a patient.

FIG. 7 is an exemplary screen display 700 that may be seen by the user during a session with a patient. A patient device-side view 710 may show live streaming video of the patient recorded by the telepresence device. A control device-side view 720 may show video of the user captured by the control device and sent to the telepresence device for display to the patient. The control device and telepresence device may enable live, visual interaction between the patient and a medical practitioner and may allow the medical practitioner to diagnose and/or treat the patient from a remote location. A plurality of tabs 701, 702, 703 may allow the user to select between a pre-session loop interface, an active session interface, and a historical session interface, respectively.

A plurality of pre-session loops 730 may be displayed to the user when the pre-session loop tab 701 is selected. The pre-session loops 730 may include video of key elements, such as the patient's face, an EKG monitor, other monitors, a chart, fluid bags, etc., that may be of interest to a medical practitioner immediately upon connecting with the telepresence device. The pre-session loops 730 may contain important visual information that would otherwise be obtained by manually manipulating a camera to view each area of interest. Some visual information, such as facial pallor and/or fluid level/color, may not be available through standard telemetry systems. Accordingly, the pre-session loops 730 may supplement telemetry data received by the medical practitioner. In some situations, telemetry data may not be transmitted to the medical practitioners, so the pre-session loops 730 may be required to see the telemetry data as well.

The pre-session loops 730 may be generated by the telepresence device by recording short videos of areas of interest before the user connects to the telepresence device. In some embodiments, the telepresence device may be notified of which patient to visit before the medical practitioner connects. The telepresence device may receive an indication to navigate to an indicated location, such as a patient's room. The telepresence device may travel to the indicated location and face the patient's bed.

While waiting for the medical practitioner to connect, the telepresence device may scan the room by panning, tilting, and/or zooming a camera to identify the key elements. For example, the patient's face may be identified using Haar-like feature analysis, and the monitors and/or fluid bags may be identified using scale-invariant feature transform (SIFT), speeded up robust features (SURF), and/or oriented features from accelerated segment test and rotated binary robust independent elementary features (ORB). The telepresence device may zoom in on each key element, thereby targeting an area of interest and record a video clip of the area of interest for a predetermined time period (e.g., five to ten seconds). If the telepresence device is still waiting for the medical practitioner to connect after video clips of each area of interest have been recorded, the telepresence device may cycle through the area of interest again to keep the video clips as recent as possible. When the medical practitioner connects to the telepresence device, the recorded video dips may be transmitted to the medical practitioner's control device with the times when the video clips were recorded in addition to a live video feed. The time 735 and pre-session loops 730 may be displayed to the medical practitioner. The pre-session loops 730 may be repeatedly played (e.g., looped) for the medical practitioner.

Figure 8:
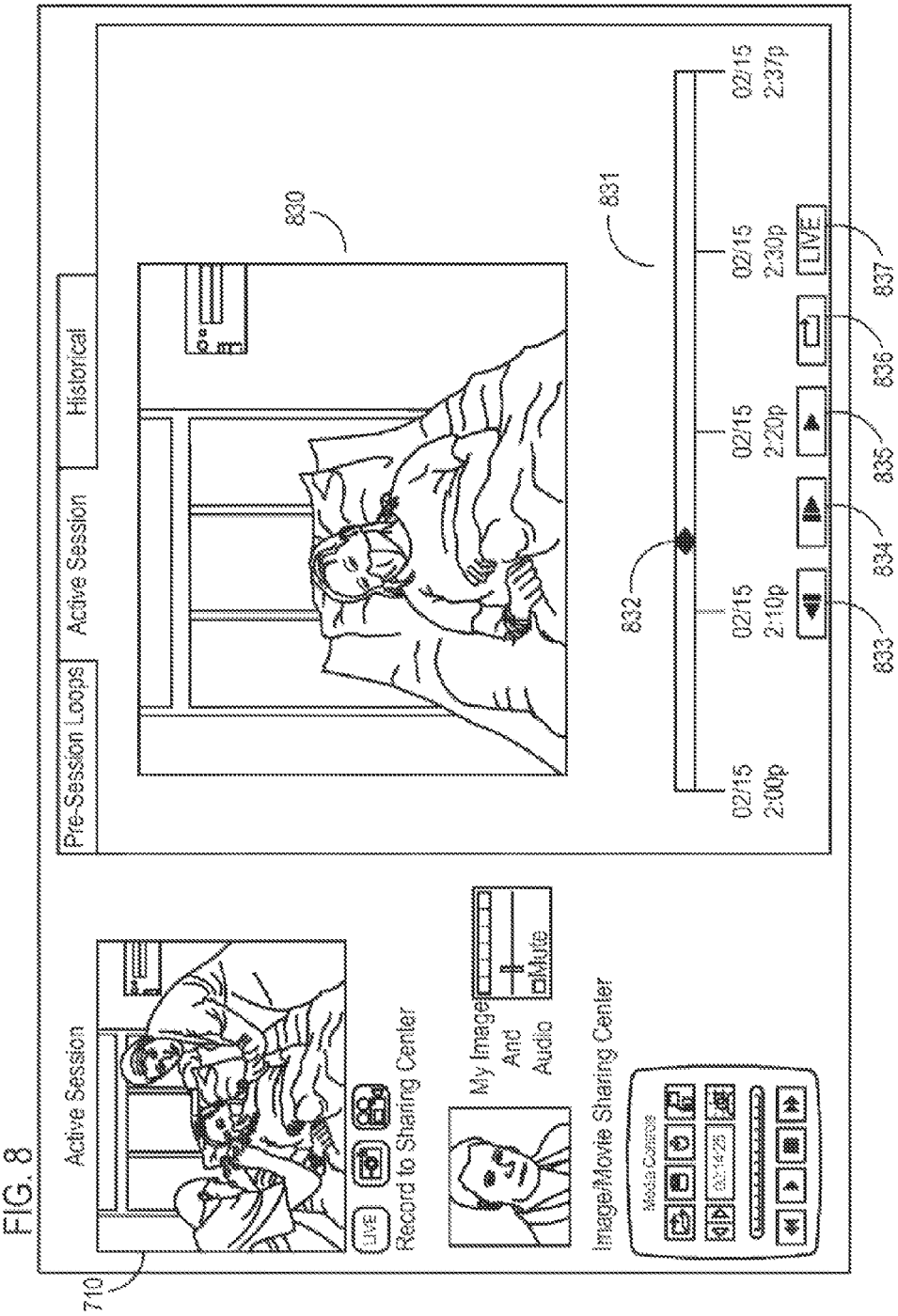
FIG. 8 is an exemplary screen display comprising one or more temporal control mechanisms.

FIG. 8 is an exemplary screen display 800 comprising one or more temporal control mechanisms 831, 832, 833, 834, 835, 838, 837. A medical practitioner may wish to quickly view historical video of a patient. For example, the medical practitioner may wish to view historical video that occurred during an active session. A timeline 831 may allow the user to select any point in a video segment recorded for the active session. The scale of the timeline 831 may change as video is recorded. The user may select a point on the timeline 831 corresponding to the time from which the user would like playback to start. In the illustrated embodiment, a diamond 832 may indicate the selected point. In an embodiment, the user may also be required to select, a play button 835 before playback starts from the selected point. The play button 835 may transform to a pause button (not shown) upon selection.

A jump-to-start button 833 may allow the user to start playback at a start of the current video segment, and a jump-to-end button 834 may allow the user to start playback at an end of the current video segment. A LIVE button 837 may cause live video to start playing in an upper video window 830. In some situations, the upper video window 830 will display a larger view of the patient device-side view 710. However, if media, such as an educational video, is being shared with the patient, the patient device-side view 710 may show the educational video rather than the patient. A loop button 836 may allow a section of video to be looped.

Figure 9:
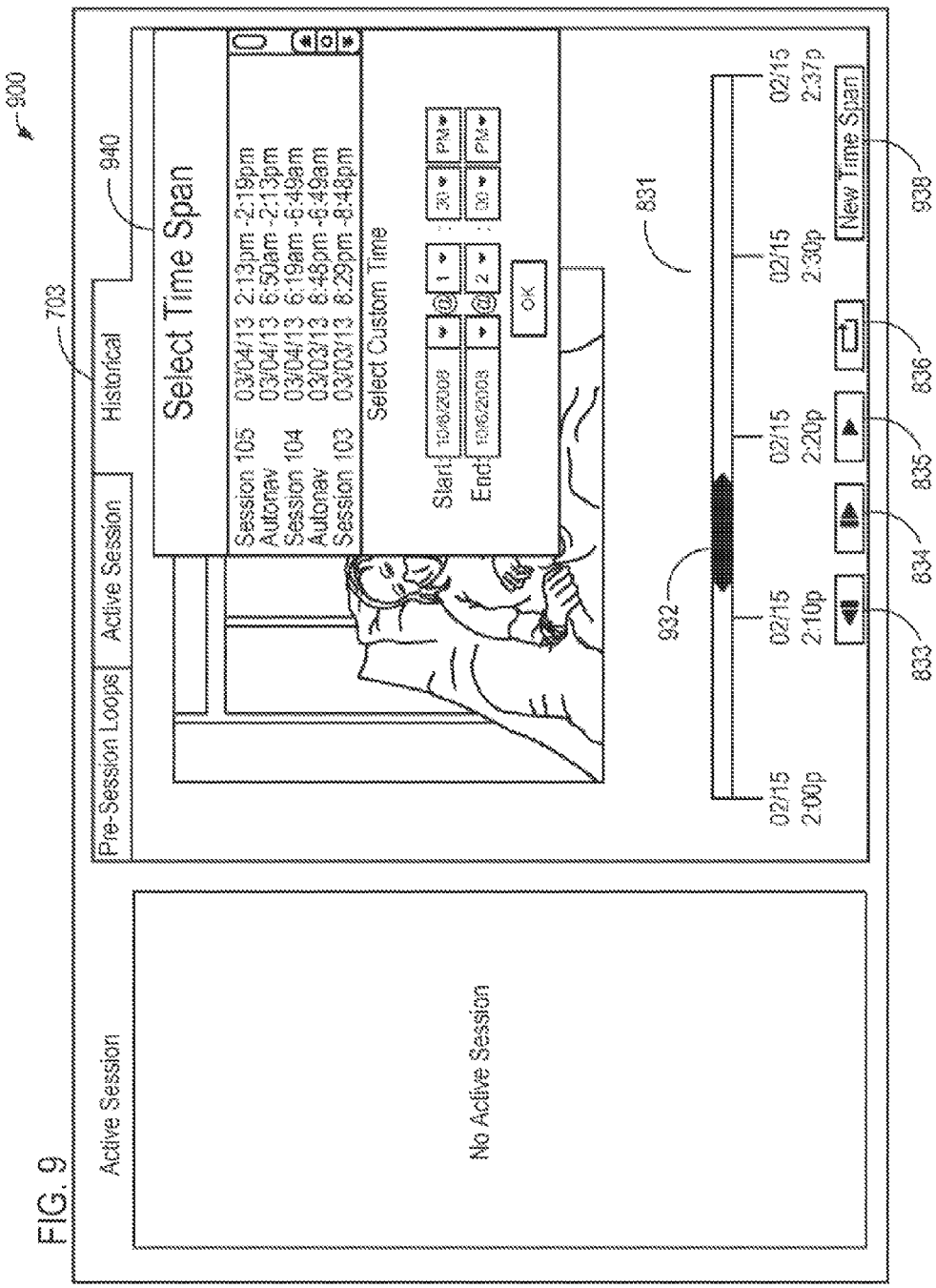
FIG. 9 is an exemplary screen display comprising one or more temporal control mechanisms for historical video segments.

FIG. 9 is an exemplary screen display 900 comprising one or more temporal control mechanisms 831, 932, 833, 834, 835, 836 for historical video segments. The historical video segment may have been recorded during a previous telepresence session, during local caregiver use of the telepresence device, and/or during autonomous off-line activities of the telepresence device. Video streamed from the telepresence device may be broken up into video segments. For example, the streamed video may be broken up based on sessions and time spent autonomously navigating off-line. When the user selects the historical tab 703, a select time span box 940 may prompt the user to select a video segment. The user may also be to select custom time spans by selecting a new time span button 938. The new time span may not wholly correspond to the existing time spans. Instead, it may be larger or smaller than the existing time spans and/or overlap with multiple existing time spans. The user may be able to interact with a new video segment corresponding to the new time span.

During either the active or the historical viewing, the user may be able to click and drag on the timeline 831 to select a span of time. In the illustrated embodiment, the span of Lime may be indicated by an elongated diamond 932. The user may select play button 835 or the play loop button 836 to pay the selected span of time once or repeatedly, respectively. In some embodiments, the play loop button 836 may be disabled unless a span of time is selected. Looped video may be helpful, for example, when a medical practitioner is trying to review and analyze video of an EKG monitor.

Figure 10:
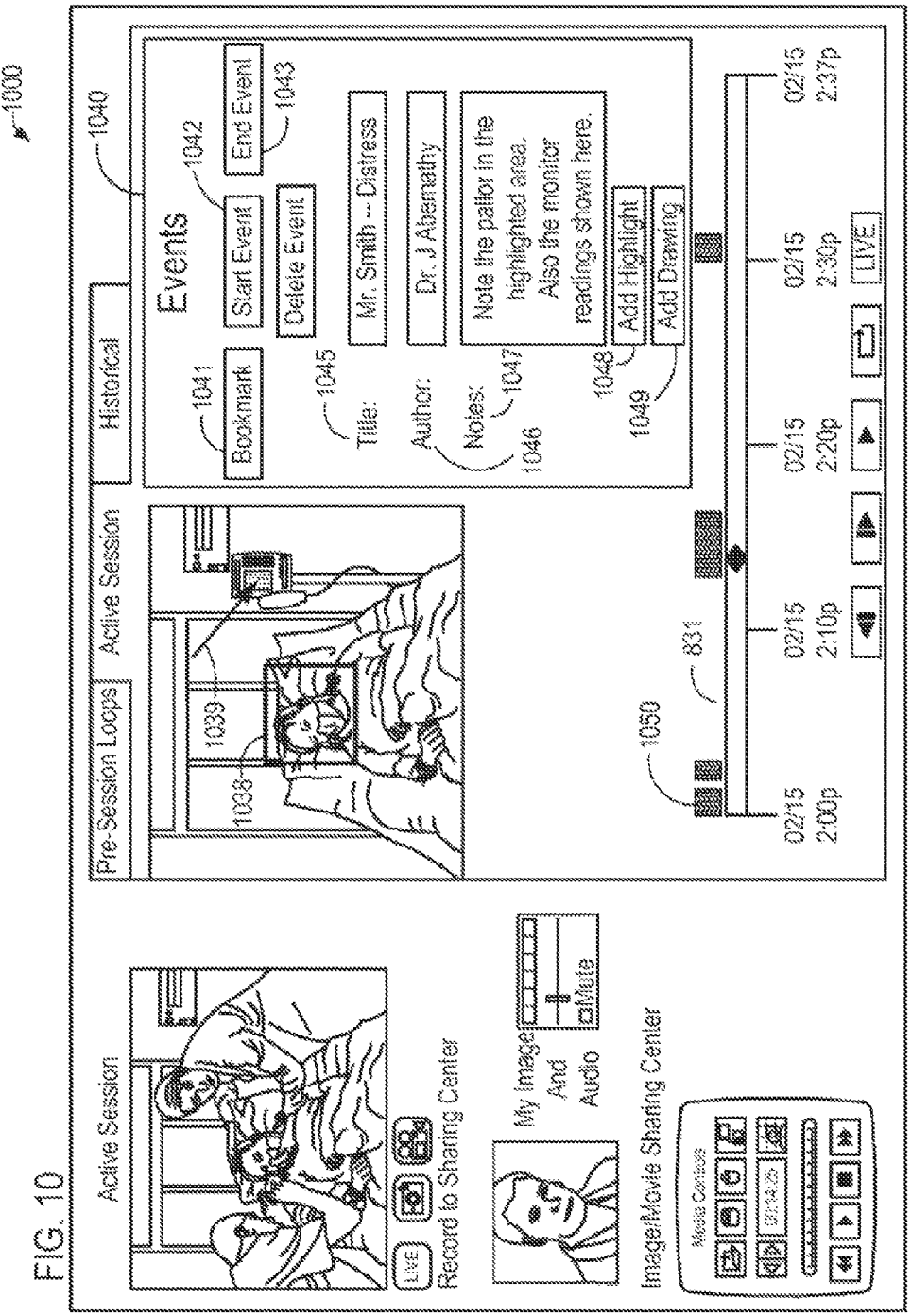
FIG. 10 is an exemplary screen display with an event added to a video segment.

FIG. 10 is an exemplary screen display 1000 with an event 1040 added to a video segment. The event 1040 may be added to the video segment by a user live during a session and/or during historical payback. The event 1040 may be an annotation, such as text, a drawing, a marking, etc. Annotations may be overlaid on the video segment. Other users may be able to add notes to an annotation after creation, and an indication of who added each note may be saved. The user may be able to add the event 1040 by selecting a start event button 1042 or a bookmark button 1041. The user may select the time span for the event 1040 by selecting an end event button 1043 at a time in the video when the event 1040 should end. For bookmarks, a default length of time may be used to determine when the event 1040 ends.

The user may be able to input a title 1045 and notes 1047 for the event as text. An add highlight button 1048 may allow the user to draw a box 1038 over the video, and an add drawing button 1049 may enable a drawing function when the cursor is over the video (e.g., allowing user to draw an arrow 1039). The drawings and/or highlighting may be visible only when the time span of the event. Similarly, the title and/or notes may be associated in memory with the time span, so they are only displayed during the time span and/or so it can be indicated to the user that they are associated with that time span. In an embodiment, the author 1046 for the event is automatically completed with the user's name. The author 1046 may be the original creator of the event 1040. Notes, drawings, and highlighting from other staff may be separately tagged to indicate who added them.

In an embodiment, rectangles 1050 with rounded edges may indicate events. The rectangles 1050 may be located just above the timeline 831 and the length of each rectangle may correspond to the time span of each event. A user may be able to select rectangle 1050 to view the corresponding event. Hovering over the rectangle 1050 may cause a balloon or callout to display the title, if any, of the corresponding event. In other embodiments, various interactive indications may be used to alert the user to saved events.

Figure 11:
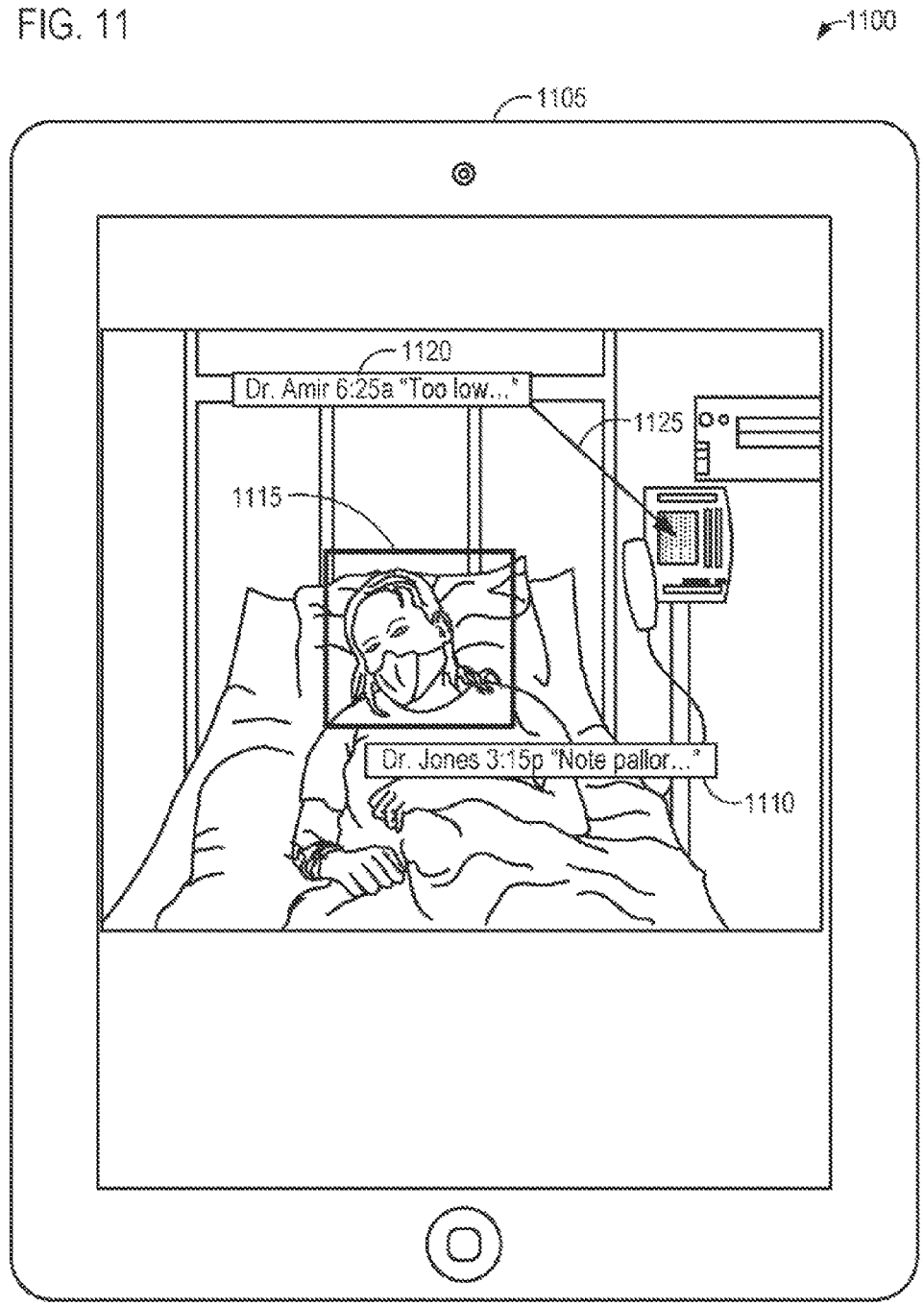
FIG. 11 is an exemplary screen display on a control device during recall of notes, drawings, and/or highlights made during a predetermined time period.

FIG. 11 is an exemplary screen display 1100 on a control device 1105 during recall of notes 1110, 1120, drawings 1125, and/or highlights 1115. A second healthcare practitioner may wish to see all notes 1110, 1120, drawings 1125, and/or highlights 1115. The second healthcare practitioner may view live video of a patient fumed using a rear camera (not shown) of the control device 1105, and the notes 1110, 1120, drawings 1125, and/or highlights 1115 for the patient may be automatically displayed on the video. Authors and timestamps for each note 1110, 1120, drawing 1125, and/or highlight 1115 may be displayed. In an embodiment, the second healthcare practitioner may specify that annotations from only certain authors and/or with timestamps in a predetermined range should be viewed.

In an embodiment, when an event is created by a first user, first location data for video to which the event was added may be stored. For example, the room number where the video was taken, the position and/or orientation of the telepresence device, the pan, tilt, and/or zoom of a camera, and/or a set of image descriptors used for pattern matching (e.g., from SIFT, SURF, ORB, or the like) may be saved as the first location data. Position and/or orientation data may be extracted from the navigation system of the telepresence device, and pan, tilt, and/or zoom information may be extracted from encoders in the camera or head of the telepresence device. In an embodiment, the first location data may correspond to the location being viewed rather than the location from which images and/or video were recorded. For example, the annotation may be associated with a specific object within an image and the first location data may describe the location of the object.

The second user may input general location or position information, such as a room number, to narrow searching and point the rear camera of the control device 1105 at a desired area to capture a picture and/or video. Second location data may be generated from pattern matching of an image, such as a video frame, captured by rear camera and/or from the user-selected room number. Scale-invariant feature matching of the image may determine whether the first and second location data are within the predetermined threshold. If the second location data is within a predetermined threshold of the first location data, the notes 1110, 1120, drawings 1125, and highlights 1115 or an abbreviated form thereof (e.g., a preview) may be displayed.

Alternatively, or in addition, when using a telepresence device with a robotic platform/base, for example, inverse kinematics may be used to match a current position/orientation/pan/tilt/zoom image framing with the image framing when an annotation and associated position, orientation, pan, tilt, and/or zoom data were stored. In an embodiment, both scale-invariant pattern matching and inverse kinematics may be used for increased robustness. While the results of each algorithm may be noisy, the system may utilize Kalman filtering on the redundant data streams to determine most likely positions.

Figure 12:
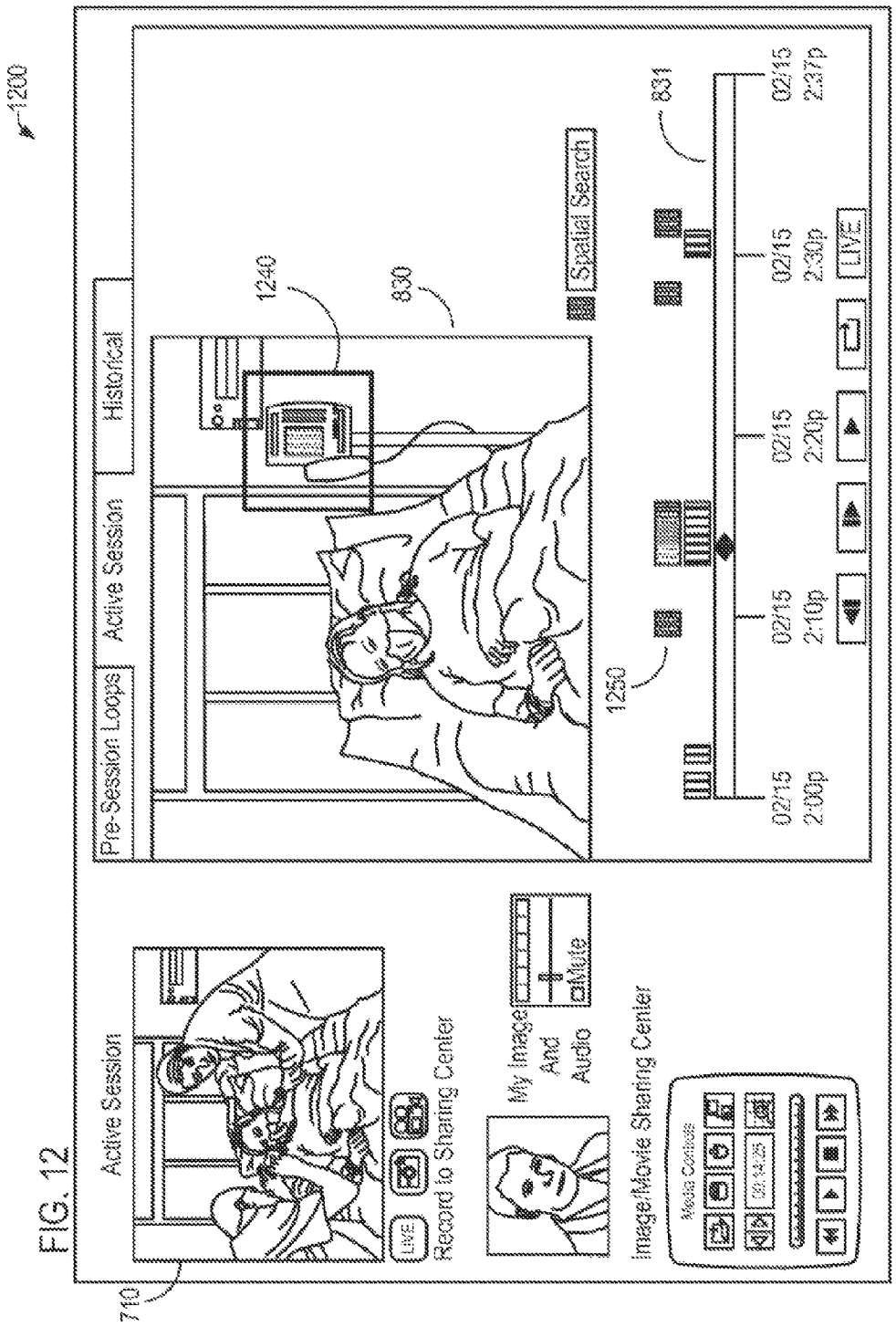
FIG. 12 is an exemplary screen display showing spatial searching of a video segment.

FIG. 12 is an exemplary screen display 1200 showing spatial searching of a video segment. A user may wish to search a video for an object contained in a frame of the video to determine when in the video that object appears. For example, a medical practitioner may want to view all footage of a patient monitor, fluid beg, or body part of the patient to see how the readings, fluid color, or patient pallor has changed over time. The user may be able to draw a box 1240 around an area of interest in a video frame while the video is paused. Inverse kinematics and/or pattern matching from image descriptors may be used to identifying portions of the video correlated with the area of interest.

A layer 1250 above the timeline 831, for example, may indicate matches. The layer 1250 may comprise a plurality of rectangles corresponding to each time the area of interest appeared. The layer 1250 may indicate ratings for each match based on the relative size of the area of interest in each match. In an embodiment, the rating may correspond to a color brightness at each location in the layer 1250 with a brighter color indicating a larger size in the match. In a configuration, the user may review the matches in the upper video window 830 while watching the area of interest live in the patient device-side view 710.

In an exemplary use, a healthcare practitioner may review a video of a surgery to determine what occurred at a certain spot on the patient. In another exemplary application, a healthcare practitioner may believe a patient's EKG has changed recently but is unsure. A spatial search on the EKG may indicate previous time spans when a camera was recording the EKG. In an industrial example, telepresence device may have inspected various objects in a remote scene over a protracted time period. A user may wish to examine a close-up image of a counterbalance reel but does not want to search video for the entire protracted time period. The user can draw a box around the counterbalance and the system may find the relevant portions of the video.

Figure 13:
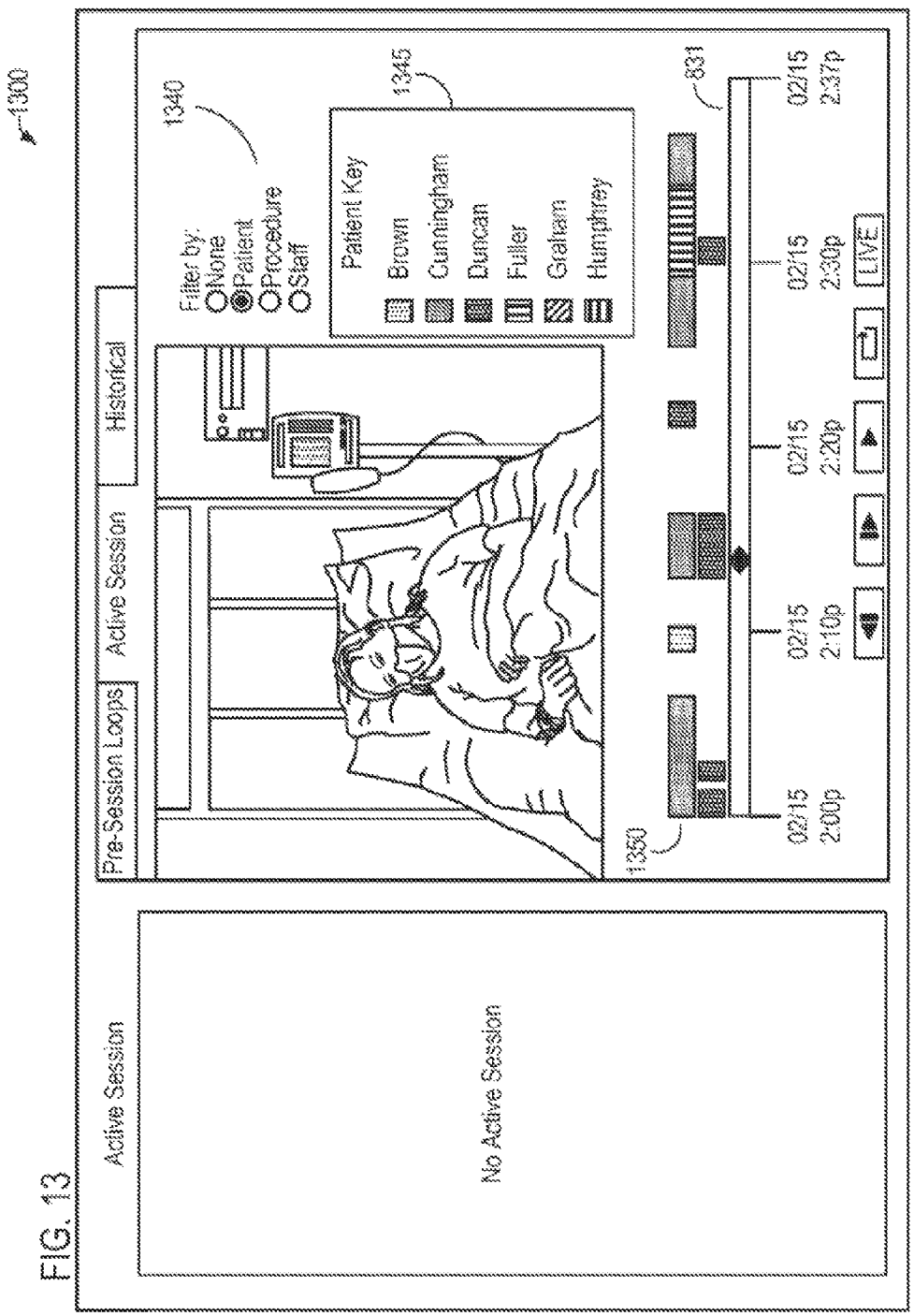
FIG. 13 is an exemplary screen display of results from a contextual search.

FIG. 13 is an exemplary screen display 1300 of results 1350 from a contextual search. Various situational data may be identified by the telepresence device and stored with recorded video. The situational data may include a room number, patient name, patient complaint, procedure being performed, healthcare practitioner operating the telepresence device, and the like. The situational data can be used to search the recorded video for video segments matching a situation of interest. For example, a reviewing healthcare professional may wish to see all past video of a patient; stored videos of certain procedures may be used for training; and/or videos where a particular healthcare professional was operating the telepresence devices may be used to provide feedback. In an embodiment, the telepresence device may know the room number for a video segment but not the patient name or procedure. A healthcare practitioner may input a procedure being performed and/or a patient name and a corresponding room number for the procedure or patient name. The input may be used to map the room number to the patient name or procedure.

A filter criterion 1340 may be used to identify video segments according to situational data elements corresponding to the filter criterion 1340. For example, a healthcare practitioner may specify a filter criterion 1340 of patient, and the video segments may be identified by patient name. In an embodiment, a key 1345 may specify a color corresponding to each unique situational data element. The results 50 may comprise a layer above the timeline 831 including one or more rectangles containing colors from the key 1345. In an embodiment, hovering over any of the one or more rectangles in the results 1350 may cause a balloon or callout text to display the value of the situational data element.

A telepresence device may be configured to provide synchronized location and video replay. For a mobile telepresence device, such as a telepresence device with a robotic base, a local or remote user may desire for the telepresence device to retrace a previous route and play back video recorded while traversing that route. For example, a healthcare practitioner may have missed group rounds and wish to visit each patient via the telepresence device while seeing what occurred during group rounds. In such an example, the telepresence device may have been configured to follow a group of people during group rounds without a remote user controlling the telepresence device. During the autonomous following, the telepresence robot may actively record both a video stream from the camera and position and orientation data from the navigation system, synchronized with the video stream. In an embodiment, a trace route button (not shown) may be available during playback of a recorded video. In response to the trace route button being selected, the telepresence device may access stored position and/or orientation data to determine a location and/or route corresponding to the video being played back.

In an embodiment, the video may be paused with a message "Driving to video position" overlaid on the video while the telepresence device navigates to the location corresponding to a current playback position in the video. When the telepresence device arrives at the location, video playback may resume and/or the telepresence device may begin retracing the route corresponding to the video. The user may be able to pause the video, which may also pause movement of the telepresence device. While the video is paused, the user may control the telepresence device and interact using live video with, for example, other healthcare practitioners and/or patients. When the user presses play, the telepresence device may automatically return to the position where it was paused and continue playback and corresponding navigation. The user may be able to add notes, drawings, and/or highlights to the recorded video.

The telepresence device may be configured to attempt to stay within a first predetermined distance of the location and/or route corresponding to the current playback position in the video (e.g., the position during original recording). If the telepresence device is more than the first predetermined distance from the location and/or route, the video may be paused and a message "Catching up to video position" may be overlaid on the video. Once the telepresence device is within a second predetermined distance of the location and/or route, playback may resume. The second predetermined distance may be smaller than the first predetermined distance to create a hysteresis loop. For example, playback may stop when the telepresence device is more than ten feet from the desired position and resume when the telepresence device returns to less than five feet from the desired position.

FIG. 14 is an exemplary screen display 1400 of a series of stored trend videos 1452, 1454, 1456 for a plurality of areas of interest. Diagnoses and/or treatment of a patient by a healthcare practitioner may be improved comparing imagery over time. For example, the healthcare practitioner may look for changes in the pallor, fluid color or level, and/or various monitors attached to the patient.

In an embodiment, the telepresence device may be configured to autonomously visit a plurality of patients on a pre-defined schedule. For each patient, the telepresence device may scan the room for pre-defined areas of interest using, for example, a built-in camera. For example, the telepresence may attempt to recognize the patient's face, one or more monitors, fluid bags, and the like using Haar-like feature matching, SIFT, SURF, ORB, and/or the like. For each area of interest identified, the telepresence device may zoom a camera on the area of interest and record video for a predetermined time period (e.g., ten seconds). The recorded video may be stored by the telepresence device and/or a server. A corresponding time stamp may also be stored with the recorded video. The telepresence device may proceed to the next patients mom after the video has been recorded.

A control device may load and display a series of stored trend videos 1452, 1454, 1456 when the user selects a trending tab 1404. Each video may play for the predetermined time period automatically and/or after manual selection. A corresponding time stamp 1442, 1444, 1446 may be displayed for each set of videos 1452, 1454, 1456 in the series to inform the user when the video was recorded. In an embodiment, the user may be able to enlarge a video to full size by double-clicking on it.

Figure 15A:
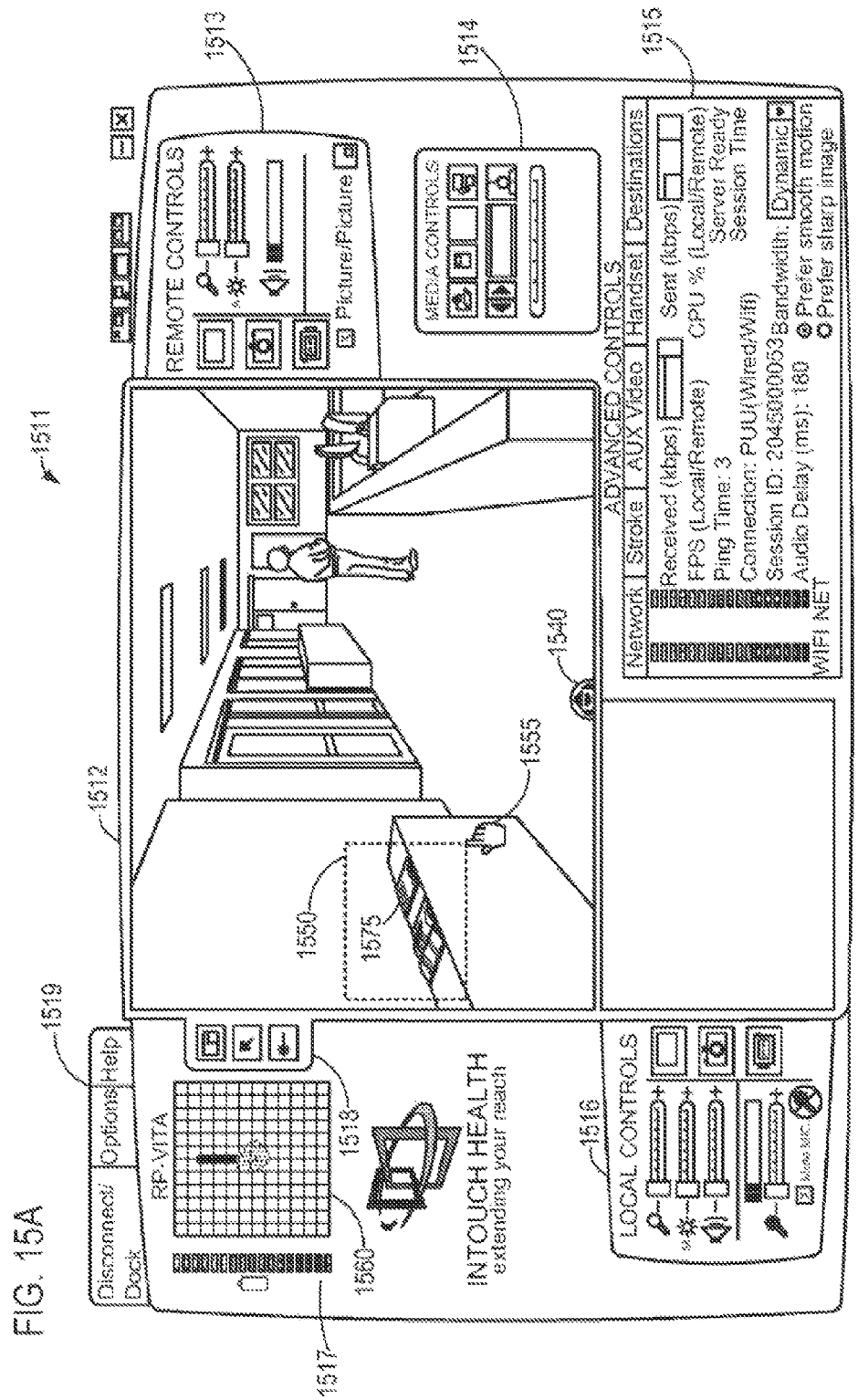
FIG. 15A illustrates a box drawn within a video feed to zoom/magnify portion of the video feed.

FIG. 15A illustrates a control device 1511 with a box 1550 drawn within a video feed 1512 to zoom in on a portion of the video feed 1512. As illustrated in FIG. 15A, the control device 1511 may include a four way controller 1540 selectively overlaid on the live video feed 1512. Various additional panels, icons, tabs, and/or other objects 1513, 1514, 1515, 1516, 1517, 1518, and 1519 may be selectively displayed. Any of a wide variety of functional icons, buttons, drive modes, maps, and/or other panels, windows, and/or objects described herein may be displayed or selectively displayed in conjunction with the zoom box 1550 functionality.

An operator may indicate a desired zoom region by creating a box 1550 around a portion of the video feed 1512. Alternatively or additionally, an operator may simply click a center of a desired region, define a region using a touch input, define a region using a cursor 1555, and/or otherwise select a portion of the video feed 1512. In the illustrated embodiment, the portion selected includes printed materials containing informational content. A zoom function of any type, including the illustrated box zoom 1550, may be used to zoom in on any portion of the video teed 1512.

Figure 15B:
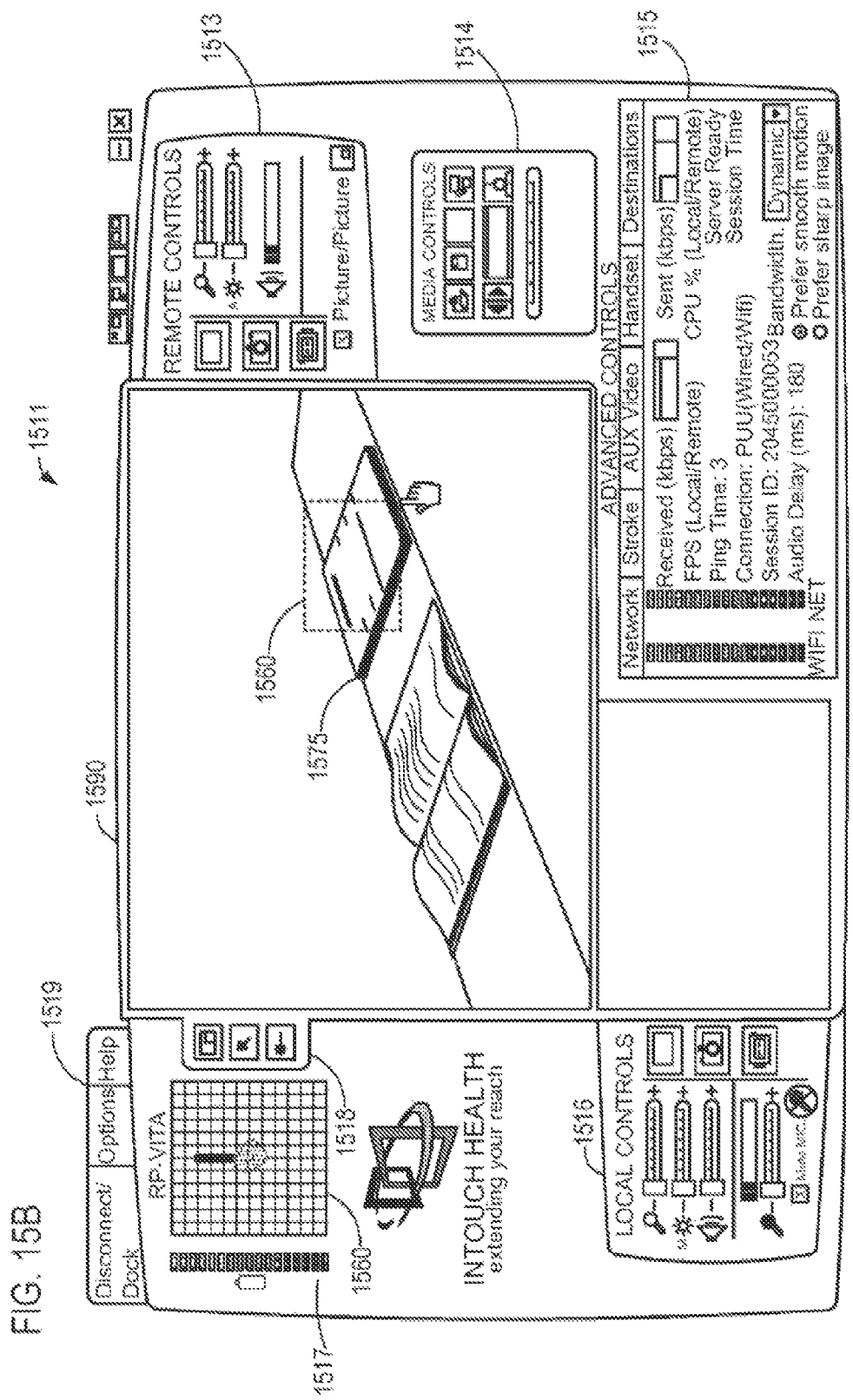
FIG. 15B illustrates a zoomed view of the video feed with a second box drawn for additional zooming on a document.

FIG. 15B illustrates a zoomed view 1590 of the video feed 1512 (FIG. 15A) with a second box 1560 drawn for additional zooming on a document 1575. A zoom request may be generated using any of a wide variety of selection methods for selecting a portion of the zoomed view video feed 1590. In the illustrated embodiment, a zoom request is made by defining another box 1560. A zoom request may cause the selected portion of the video feed 1590 to be magnified. Magnifying the video feed may be performed in any number of ways, including transmitting instructions to adjust an optical zoom of a camera of the telepresence device, digitally zooming the selected portion 1560 of the video feed 1590 and/or transmitting navigation instructions to the telepresence device to cause the telepresence device to navigate in the direction of the selected portion 1560 of the video feed 1590.

FIG. 15C illustrates a zoomed view 1595 of the document 1575. The text of the document 1575 may not be perfectly aligned with the camera of the telepresence device. Accordingly, the text, images, charts, etc, of a document or other information content may be misaligned with respect to the orientation of the video feed. For example, the text, images, charts, etc. may be at an angle relative to the video feed 1585 and/or skewed due to the relative angle of the informational content. According to various embodiments, the control device 1511 may be configured to automatically align the informational content within a video feed 1512, 1590, and 1595.

Initially, objects that potentially have information content of interest may be identified, such as telemetry monitors, hospital signs, patient charts, lab results on a nursing station, room numbers, or the like. Objects of interest may be identified by automatically recognizing shapes that correspond to objects of interest. Uninteresting objects may share similarities with objects of interest, so color, shape, position, and/or user preferences may be used to learn to differentiate objects of interest from uninteresting objects. Alternatively, or in addition, objects of interest may be identified using trained SIFT features. Detected objects of interest may be leveraged for other purposes, such as to assist navigation and/or automatically create waypoints during map generation). For example, room numbers and/or wall paintings may be recognized for navigation and/or to build waypoints. Room numbers may be used to automatically create waypoints and a corresponding structured list of user-available waypoints.

In an embodiment, potential objects of interest may be highlighted and/or outlined in the received video, and the user may select an object for alignment. Alternatively, or in addition, the telepresence device, server, and/or control device may automatically determine whether or not an object should be aligned. In some embodiments, the informational content may not be automatically aligned unless the information content comprises a sufficient portion of the displayed content within a video feed 1512, 1590, and 1595. Alternatively, the informational content may be automatically aligned only if it would be legible within the video feed 1512, 1590, and 1595. For example, in FIG. 15A, the information content (the document 1575) may not comprise a sufficient portion of the video feed 1512 to be automatically aligned, while the same document 1575 in the zoomed view 1595 of FIG. 15C would be automatically aligned. To align the information content, the system may identify the four salient edges of the object using, for example, Hough line detection, and thereby identify the corners of the information content. Once the corners are identified, the system may automatically rotate and/or deskew the image of the object for display. In an embodiment, the identified corners may be mapped to predetermined and/or corresponding aligned locations, such as the corners of a rectangle, and the area inside the corners may be correspondingly adjusted. The user may be able to resize the length, width, and/or both for the deskewed image. Alternatively, or in addition, information content may be converted to text, such as using optical character recognition (OCR).

In an alternative embodiment, the document 1575 (or other information content, such as an electronic display or patient monitor) may not be automatically aligned. Rather, the information content may be selectively (though automatically) aligned based on a user selection and/or be manually aligned through one or more manual alignment tools (e.g., a rotate function, a deskew function, and/or a function allowing the user to identify corners of the information content).

Alternatively, or in addition, the position and/or orientation of the telepresence device may be modified relative to the information content. The telepresence device may be brought directly in line with the information content to align the information content. A position of the information content may be computed using pixel mapping and/or the pan, tilt, and/or zoom of the camera. The information content position may be projected onto a two dimensional plane parallel to or coincident with the floor. The orientation of the information content may be determined (e.g., using OCR), and a line and/or ray in the two dimensional plane corresponding to the orientation and intersecting the projected information content position may be computed. The point of the line may be lined up positions to which the robot may move to view aligned information content (e.g., the two dimensional plane may correspond to possible positions to which the telepresence device can navigate, and the line may correspond to points where the information content may be aligned when viewed). The telepresence device may be directed (and/or may decide) to navigate to the closest unobstructed point and/or the closest unobstructed point exceeding a minimum distance. The line and/or two dimensional plane may also be used to orient the telepresence device directly towards the information content once the telepresence device has navigated to the desired location.

Figure 15D:
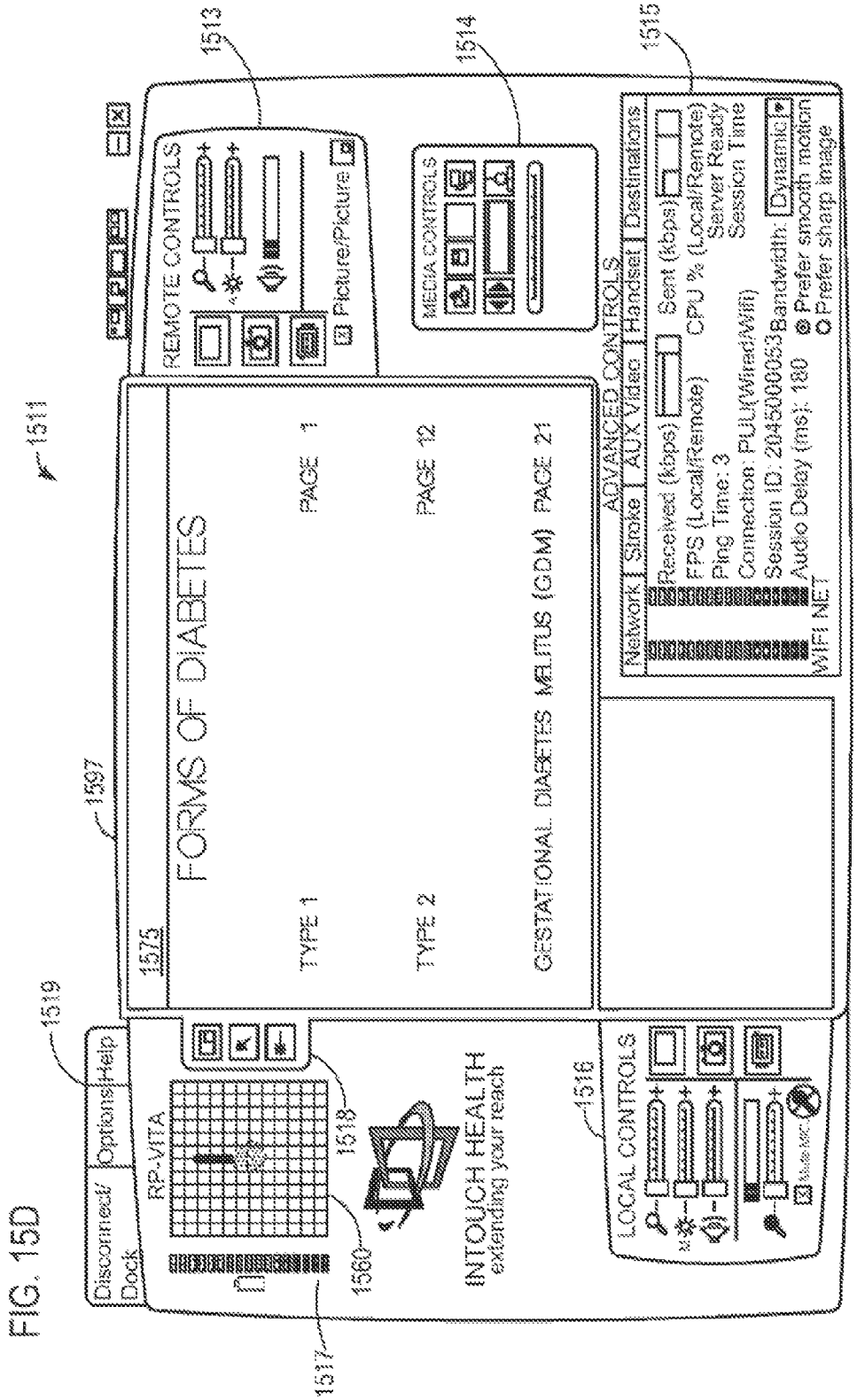
FIG. 15D illustrates a zoomed view of the document with the text deskewed and rotated.

FIG. 15D illustrates a zoomed view 1597 of the document 1575 with the text deskewed and rotated. Comparing FIGS. 15C and 15D, it is apparent that the digitally aligned text in Ha 150 is easier to read than the actual (misaligned) zoomed view 1595 of the document 1575 in FIG. 15C. In various embodiments the informational content may comprise documents, charts, images, text, and/or other informational material. The information content may be physically displayed and/or electronically displayed. In some embodiments, the informational content may be further enhance such as, for example, by adjusting the contrast of the informational content.

In some embodiments, informational content displayed on an electronic display captured by a camera of a telepresence device and displayed by the control device may have various video artifacts, such as scrolling bars or darker sections due to unsynchronized refresh rates. Accordingly, the control device 1511 may automatically synchronize refresh rates and/or otherwise compensate for unsynchronized refresh rates in order to improve the display of electronically displayed informational content.

According to various embodiments, a telepresence and/or control device may be configured with ail or some of the features and embodiments described herein. For example, a telepresence and/or control device may include any number of the features and embodiments described herein as selectively displayed and/or selectively functional options. An explicit enumeration of all possible permutations of the various embodiments is not included herein; however, it will be apparent to one of skill in the art that any of the variously described embodiments may be selectively utilized, if not at the same time, in a single telepresence and/or control device.

It will be understood by those having skill in the art that many changes may be made to the details of the above-described embodiments without departing from the underlying principles of the disclosure. The scope of the present disclosure should, therefore, be determined only by the following claims.

The invention claimed is:

1. A non-transitory computer-readable storage medium including computer-readable instruction code for performing a method of generating pre-session video loops, the method comprising:
   receiving, at a telepresence device that includes a camera, a display device, a microphone, and a speaker, an indication to navigate to an indicated location;
   adjusting a camera on the telepresence device to identify one or more areas of interest at the indicated location;
   sequentially targeting each area of interest with the camera;
   recording video of each area of interest for a predetermined time period; and
   transmitting the recorded video to a remotely located control device, wherein the control device can establish a two-way audio/video communication session with the telepresence device.

2. The non-transitory computer-readable storage medium of claim 1, wherein recording video of each area of interest comprises continuously cycling through the one or more areas of interest until receiving a connection request from the remotely located control device.

3. The non-transitory computer-readable storage medium of claim 1, wherein the one or more areas of interest contain an object selected from the group consisting of a patient's face, an EKG monitor, a chart, and a fluid bag.

4. The non-transitory computer-readable storage medium of claim 1, wherein the method further comprises recording a time code indicating when the video of the one or more areas of interest was recorded.

5. A non-transitory computer-readable storage medium including computer-readable instruction code for performing a method of providing segmented temporal video control of video received from a telepresence device that includes a camera, a display device, a microphone, and a speaker, the method comprising:
   receiving, at a control device, streaming video from the telepresence device;
   determining a plurality of video segments corresponding to a plurality of telepresence device activities;
   displaying a first video segment associated with a first telepresence device activity to a user; and
   providing a temporal control mechanism to the user permitting the user to select a first playback point within the first video segment, wherein the control device can establish a two-way audio/video communication session with the telepresence device.

6. The non-transitory computer-readable storage medium of claim 5, wherein the method further comprises receiving an indication of a desired video segment from the user.

7. The non-transitory computer-readable storage medium of claim 5, wherein the method further comprises: receiving an indication of a desired time span from the user, wherein none of the plurality of determined video segments wholly correspond to the desired time span; determining a desired video segment corresponding to the desired time span; and displaying the desired video segment to the user.

8. The non-transitory computer-readable storage medium of claim 7, wherein the method further comprises receiving an indication from the user to play the desired video segment in a loop.

9. A non-transitory computer-readable storage medium including computer-readable instruction code for performing a method of annotating video segments received from a telepresence device that includes a camera, a display device, a microphone, and a speaker, the method comprising:
   receiving, at a control device, streaming video from the telepresence device;
   displaying a video segment from the streaming video to a user;
   receiving an indication of a desired time span from the user;
   receiving an annotation corresponding to the desired time span from the user;
   storing the received annotation in association with the desired time span; and
   displaying an interactive indication in a location corresponding to the desired time span, wherein the user may access the received annotation using the interactive indication, wherein the control device can establish a two-way audio/video communication session with the telepresence device.

10. The non-transitory computer-readable storage medium of claim 9, wherein receiving an indication of a desired time span comprises: receiving a user indicated start time; and automatically selecting an end time based on a default time span length.

11. The non-transitory computer-readable storage medium of claim 9, wherein receiving an annotation comprises: receiving a user indicated title and a user indicated note; and automatically inserting an author name into the annotation, wherein the author name corresponds to the user.

12. The non-transitory computer-readable storage medium of claim 9, wherein the method further comprises: receiving a drawn object to be overlaid on the video segment during the desired time span; and displaying the drawn object overlaid on the video segment when the desired time span is displayed.

13. A non-transitory computer-readable storage medium including computer-readable instruction code for performing a method of recalling annotations based on a captured image, the method comprising:
   receiving, at a control device, video from a telepresence device that includes a camera, display device, a microphone, and a speaker;
   receiving an annotation from a first user corresponding to a frame in the video;
   storing first location data corresponding to the frame;
   storing the annotation;
   receiving an image from a second device at a later time;
   identifying second location data corresponding to the image;
   retrieving the first location data and the annotation; and
   displaying at least a portion of the annotation if the second location data is within a predetermined threshold of the first location data, wherein the control device can establish a two-way audio/video communication session with the telepresence device.

14. The non-transitory computer-readable storage medium of claim 13, wherein the first location data comprises at least one data element selected from the group consisting of a room number, a position of the telepresence device, an orientation of the telepresence device, a camera tilt, a camera pan, a camera zoom, and a set of image descriptors, and wherein the first location data corresponds to the frame in the video.

15. The non-transitory computer-readable storage medium of claim 13, wherein the first location data comprises general position information and a set of image descriptors.

16. The non-transitory computer-readable storage medium of claim 13, wherein receiving an annotation comprises receiving an annotation corresponding to an object in the frame, and wherein displaying comprises displaying at least the portion of the received annotation if a second set of image descriptors are within the predetermined threshold of a first set of image descriptors corresponding to the object.

17. The non-transitory computer-readable storage medium of claim 13, wherein the telepresence device comprises a robotic platform, wherein the first location data includes position and orientation data determined by a telepresence device component, and wherein inverse kinematics is used to compare the first location data to the second location data.

18. A non-transitory computer-readable storage medium including computer-readable instruction code for performing a method of spatially searching video, the method comprising:
  receiving, at a control device, the video from a telepresence device that includes a camera, a display device, a microphone, and a speaker;
  storing the video;
  receiving an indication of a spatial area of interest in a frame of the video from a user;
  identifying one or more video segments from the stored video containing the spatial area of interest; and
  providing indications of the one or more video segments to the user, wherein the control device can establish a two-way audio/video communication session with the telepresence device.

19. The non-transitory computer-readable storage medium of claim 18, wherein identifying one or more video segments comprises comparing the spatial area of interest to the stored video using an algorithm selected from the group consisting of a pattern-matching algorithm and an inverse kinematics algorithm.

20. The non-transitory computer-readable storage medium of claim 18, wherein identifying one or more video segments comprises determining whether a zoom level exceeds a predetermined threshold.

21. The non-transitory computer-readable storage medium of claim 18, wherein the method further comprises providing a rating for each of the one or more video segments to the user, wherein the rating is determined based on a size of the spatial area of interest in each of the one or more video segments.

22. A non-transitory computer-readable storage medium including computer-readable instruction code for performing a method of contextually searching video from a telepresence device that includes a camera, a display device, a microphone, and a speaker, the method comprising:
  receiving, at a control device, the video from the telepresence device;
  storing the video;
  storing situational data for each of a plurality of video segments;
  receiving an indication of a situation of interest from a user;
  identifying one or more matching video segments corresponding to the situation of interest; and
  providing indications of the one or more matching video segments to the user, wherein the control device can establish a two-way audio/video communication session with the telepresence device.

23. The non-transitory computer-readable storage medium of claim 22, wherein the situational data comprises at least one data element selected from the group consisting of a patient name, a procedure being performed, and a remote practitioner operating the telepresence device.

24. The non-transitory computer-readable storage medium of claim 22, wherein the method further comprises: receiving a location-situation mapping from a local practitioner; and determining the situational data from location data.

25. The non-transitory computer-readable storage medium of claim 22, wherein receiving an indication of a situation of interest comprises receiving a filter criterion, and wherein providing indications comprises providing indications identifying each video segment according to a situational data element corresponding to the filter criterion.

26. A non-transitory computer-readable storage medium including computer-readable instruction code for performing a method of synchronized location and video replay, the method comprising:
  storing a plurality of video segments recorded by a telepresence device that includes a camera, a display device, a microphone, and a speaker;
  storing corresponding location data for each of the plurality of video segments;
  navigating the telepresence device to a first location; and
  playing, at a control device, a first video segment corresponding to the first location while the telepresence device is at the first location, wherein the control device can establish a two-way audio/video communication session with the telepresence device.

27. The non-transitory computer-readable storage medium of claim 26, wherein the method further comprises receiving a pause command from a user; pausing navigation and playback in response to the pause command; and providing control of the telepresence device to the user.

28. The non-transitory computer-readable storage medium of claim 26, wherein the method further comprises pausing playback of the first video segment if the telepresence device is more than a predetermined distance from the first location.

29. The non-transitory computer-readable storage medium of claim 26, wherein the method further comprises: storing text received from a user while at the first location; and associating the text in memory with the first video segment.

30. A non-transitory computer-readable storage medium including computer-readable instruction code for performing a method of monitoring visible trends, the method comprising:
  visiting a predetermined location with a telepresence device at predetermined time intervals, the telepresence device including a camera, a display device, a microphone, and a speaker;
  scanning the predetermined location for one or more predetermined areas of interest;
  recording video of each area of interest during each visit for a predetermined time period;
  transmitting the recorded video to a storage device; and
  playing, at a control device, the recorded video, wherein the control device can establish a two-way audio/video communication session with the telepresence device.

31. The non-transitory computer-readable storage medium of claim 30, wherein scanning the predetermined location comprises identifying a face using a Haar-like feature-matching algorithm.

32. The non-transitory computer-readable storage medium of claim 30, wherein scanning the predetermined location comprises identifying an object of interest using at least one algorithm selected from the group consisting of scale-invariant feature transform (SIFT), speeded up robust features (SURF), and oriented features from accelerated segment test and rotated binary robust independent elementary features (ORB).

33. The non-transitory computer-readable storage medium of claim 30, wherein the method further comprises transmitting a time stamp corresponding to the recorded video to the storage device.

34. A non-transitory computer-readable storage medium including computer-readable instruction code for performing a method of reorienting an object in a video, the method comprising:
   establishing a two-way audio/video communication session between a control device and a telepresence device, the telepresence device including a camera, a display device, a microphone, and a speaker;
   selectively displaying a video feed from the telepresence device in a video panel on an electronic display of the control device;
   receiving a zoom request associated with a selected portion of the video feed;
   magnifying the selected portion of the video feed;
   identifying informational content within the magnified selected portion of the video feed that is misaligned with respect to the orientation of the video feed; and
   digitally aligning the informational content with respect to the orientation of the video feed.

35. The non-transitory computer-readable storage medium of claim 34, wherein magnifying the selected portion of the video feed comprises at least one of: transmitting instructions to adjust an optical zoom of a camera; digitally zooming the selected portion of the video feed; and transmitting navigation instructions to cause the telepresence device to navigate in the direction of the selected portion of the video feed.

36. The non-transitory computer-readable storage medium of claim 34, wherein identifying informational content comprises identifying informational content selected from the group consisting of written or printed information on a document, information displayed on an electronic display, text, a chart, and an image.

37. The non-transitory computer-readable storage medium of claim 34, wherein digitally aligning the informational content with respect to the video feed comprises deskewing the informational content.

38. The non-transitory computer-readable storage medium of claim 34, wherein digitally aligning the informational content with respect to the video feed comprises rotating the informational content.

39. The non-transitory computer-readable storage medium of claim 34, wherein the operations further comprise: enhancing the informational content.

40. The non-transitory computer-readable storage medium of claim 39, wherein enhancing the informational content comprises adjusting a contrast of the informational content.

41. The non-transitory computer-readable storage medium of claim 39, wherein enhancing the informational content comprises synchronizing a refresh rate of the video feed based on a refresh rate of the informational content.

* * * * *